(12) United States Patent
Gephart

(10) Patent No.: US 10,314,635 B2
(45) Date of Patent: Jun. 11, 2019

(54) TENSIONING INSTRUMENTS

(71) Applicant: A&E Advanced Closure Systems, LLC, Los Angeles, CA (US)

(72) Inventor: Matthew P. Gephart, Marquette, MI (US)

(73) Assignee: A&E Advanced Closure Systems, LLC, Los Angeles, CA (US)

( * ) Notice: Subject to any disclaimer, the term of this patent is extended or adjusted under 35 U.S.C. 154(b) by 835 days.

(21) Appl. No.: 14/724,448

(22) Filed: May 28, 2015

(65) Prior Publication Data

US 2015/0342654 A1    Dec. 3, 2015

Related U.S. Application Data

(60) Provisional application No. 62/004,022, filed on May 28, 2014.

(51) Int. Cl.
    *A61B 17/88*    (2006.01)

(52) U.S. Cl.
    CPC .............................. *A61B 17/8869* (2013.01)

(58) Field of Classification Search
    CPC ................................................ A61B 17/8869
    USPC .......................................................... 606/74
    See application file for complete search history.

(56) References Cited

U.S. PATENT DOCUMENTS

| | | |
|---|---|---|
| 1,988,534 A | 1/1935 | Abbott |
| 2,002,977 A | 5/1935 | Carr |
| 2,557,877 A | 6/1951 | Kluson |
| 3,959,960 A | 6/1976 | Santos |
| 4,050,464 A | 9/1977 | Hall |
| 4,184,784 A | 1/1980 | Killian |
| 4,269,180 A | 5/1981 | Dall |
| 4,327,715 A | 5/1982 | Corvisier |
| 4,583,541 A | 4/1986 | Barry |
| 4,959,065 A | 9/1990 | Arnett |
| 4,966,600 A | 10/1990 | Songer |
| 5,015,248 A | 5/1991 | Burstein |

(Continued)

FOREIGN PATENT DOCUMENTS

| | | |
|---|---|---|
| AU | 743254 | 12/2000 |
| CN | 201260694 Y | 6/2009 |
| DE | 7707950 U | 4/1978 |
| TW | 314764 | 9/1997 |
| WO | 9400063 | 1/1994 |
| WO | 9428812 | 12/1994 |

(Continued)

OTHER PUBLICATIONS

U.S. Appl. No. 15/645,029, filed Jul. 10, 2017, Gephart.

(Continued)

*Primary Examiner* — Si Ming Ku

(74) *Attorney, Agent, or Firm* — Fitch, Even, Tabin & Flannery LLP

(57) ABSTRACT

Instruments for applying tension to a securing device, such as a cable or wire, for securing bones in place and fastening implants, such as plates, to bones. In some forms, the tensioning instrument is configured with minimal parts for ease of manufacturing and allowing single use applications. The instrument may include a pretensioning mechanism for applying desired preload before connecting a cable to be tensioned to the instrument. The instrument may be sized and configured to remain attached to a tensioned cable while other cables are connected to a bone. In another form, the instrument may be expandable to remove any slack from the securing device and apply tension thereto.

11 Claims, 31 Drawing Sheets

(56) References Cited

U.S. PATENT DOCUMENTS

| | | |
|---|---|---|
| 5,139,498 A | 8/1992 | Astudillo Ley |
| 5,312,410 A | 5/1994 | Miller |
| 5,395,374 A | 3/1995 | Miller |
| 5,415,658 A | 5/1995 | Kilpela |
| 5,449,361 A | 9/1995 | Preissman |
| 5,456,722 A | 10/1995 | McLeod |
| 5,514,091 A | 5/1996 | Yoon |
| 5,522,827 A | 6/1996 | Combs |
| 5,536,270 A | 7/1996 | Songer |
| 5,541,380 A | 7/1996 | Ogden |
| 5,568,865 A | 10/1996 | Mase |
| 5,569,253 A | 10/1996 | Farris |
| 5,578,057 A | 11/1996 | Wenstrom, Jr. |
| 5,649,927 A | 7/1997 | Kilpela |
| 5,660,091 A | 8/1997 | Stone |
| 5,702,399 A | 12/1997 | Kilpela |
| 5,752,959 A | 5/1998 | Korhonen |
| 5,755,704 A | 5/1998 | Lunn |
| 5,788,697 A | 8/1998 | Kilpela |
| 5,810,825 A | 9/1998 | Huebner |
| 5,849,012 A | 12/1998 | Abboudi |
| 5,902,305 A | 5/1999 | Beger |
| 5,908,421 A | 6/1999 | Beger |
| 5,935,130 A | 8/1999 | Kilpela |
| 5,935,133 A | 8/1999 | Wagner |
| 5,941,881 A | 8/1999 | Barnes |
| 6,017,347 A | 1/2000 | Huebner |
| 6,077,268 A | 6/2000 | Farris |
| 6,086,590 A | 7/2000 | Margulies |
| 6,099,527 A | 8/2000 | Hochschuler |
| 6,120,506 A | 9/2000 | Kohrs |
| 6,123,709 A | 9/2000 | Jones |
| 6,277,120 B1 | 8/2001 | Lawson |
| 6,342,068 B1 | 1/2002 | Thompson |
| 6,364,885 B1 | 4/2002 | Kilpela |
| 6,378,289 B1 | 4/2002 | Trudeau |
| 6,387,099 B1 | 5/2002 | Lange |
| 6,398,787 B1 | 6/2002 | Itoman |
| 6,399,886 B1 | 6/2002 | Avellanet |
| 6,454,770 B1 | 9/2002 | Klaue |
| 6,475,220 B1 | 11/2002 | Whiteside |
| 6,494,907 B1 | 12/2002 | Bulver |
| 6,520,965 B2 | 2/2003 | Chervitz |
| 6,575,913 B1 | 6/2003 | Woolley |
| 6,595,994 B2 | 7/2003 | Kilpela |
| 6,605,091 B1 | 8/2003 | Iwanski |
| 6,629,975 B1 | 10/2003 | Kilpela |
| 6,730,091 B1 | 5/2004 | Pfefferle |
| 6,832,532 B2 | 12/2004 | Kilpela |
| 6,872,210 B2 | 3/2005 | Hearn |
| 7,052,499 B2 | 5/2006 | Steger |
| 7,156,847 B2 | 1/2007 | Abramson |
| 7,207,993 B1 | 4/2007 | Baldwin |
| 7,229,444 B2 | 6/2007 | Boyd |
| 7,250,054 B2 | 7/2007 | Allen |
| 7,494,461 B2 | 2/2009 | Wells |
| 7,635,365 B2 | 12/2009 | Ellis |
| 7,695,501 B2 | 4/2010 | Ellis |
| 7,785,355 B2 | 8/2010 | Mohr |
| 7,803,176 B2 | 9/2010 | Teague |
| 8,257,367 B2 | 9/2012 | Bryant |
| 8,282,675 B2 | 10/2012 | Maguire |
| 8,298,247 B2 | 10/2012 | Sterrett |
| 8,313,517 B2 | 11/2012 | Mohr |
| 8,337,497 B2 | 12/2012 | Deslauriers |
| 8,372,123 B2 | 2/2013 | Smisson, III |
| 8,460,295 B2 | 6/2013 | McClellan |
| 8,460,345 B2 | 6/2013 | Steger |
| 8,783,671 B2 | 7/2014 | Ranieri |
| 8,840,735 B2 | 9/2014 | Schaffer |
| 8,984,720 B2 | 3/2015 | Gephart |
| 9,216,047 B2 | 12/2015 | Bryant |
| 9,265,543 B2 | 2/2016 | Gephart |
| 9,333,021 B2 | 5/2016 | Gephart |
| 9,510,822 B2 | 12/2016 | Poucher |
| 9,510,882 B2 | 12/2016 | Dell'Oca |
| 9,561,064 B2 | 2/2017 | Goodwin |
| 2002/0072753 A1 | 6/2002 | Cohen |
| 2002/0177861 A1 | 11/2002 | Sugiyama |
| 2003/0153947 A1 | 8/2003 | Koseki |
| 2004/0138666 A1 | 7/2004 | Molz |
| 2004/0199169 A1 | 10/2004 | Koons |
| 2005/0171547 A1 | 8/2005 | Aram |
| 2005/0177179 A1 | 8/2005 | Baynham |
| 2006/0089646 A1 | 4/2006 | Bonutti |
| 2006/0155328 A1 | 7/2006 | Foerster |
| 2006/0167464 A1 | 7/2006 | Allen |
| 2006/0271060 A1 | 11/2006 | Gordon |
| 2006/0287653 A1 | 12/2006 | Rhyne |
| 2007/0225715 A1 | 9/2007 | Deffenbaugh |
| 2008/0195145 A1 | 8/2008 | Bonutti |
| 2008/0275477 A1 | 11/2008 | Sterrett |
| 2008/0287951 A1 | 11/2008 | Stoneburner |
| 2008/0306553 A1 | 12/2008 | Zucherman |
| 2009/0043316 A1 | 2/2009 | Durgin |
| 2009/0054933 A1 | 2/2009 | Mickiewicz |
| 2009/0069812 A1 | 3/2009 | Gillard |
| 2009/0069851 A1 | 3/2009 | Gillard |
| 2009/0105717 A1 | 4/2009 | Bluechel |
| 2009/0171402 A1 | 7/2009 | Dell Oca |
| 2010/0042106 A1 | 2/2010 | Bryant |
| 2010/0057091 A1 | 3/2010 | Oosterom |
| 2010/0094294 A1 | 4/2010 | Gillard |
| 2010/0094362 A1 | 4/2010 | Lutze |
| 2010/0121387 A1 | 5/2010 | Belliard |
| 2010/0179595 A1 | 7/2010 | Jackson |
| 2010/0305571 A1 | 12/2010 | Pratt |
| 2010/0318137 A1 | 12/2010 | Stucki |
| 2010/0331844 A1 | 12/2010 | Ellis |
| 2010/0331892 A1 | 12/2010 | Fell |
| 2011/0079315 A1 | 4/2011 | Norton |
| 2011/0112537 A1 | 5/2011 | Bernstein |
| 2011/0218580 A1 | 9/2011 | Schwager |
| 2011/0224676 A1 | 9/2011 | Dell Oca |
| 2011/0319978 A1 | 12/2011 | Schaffer |
| 2012/0016384 A1 | 1/2012 | Wilke |
| 2012/0089193 A1 | 4/2012 | Stone |
| 2012/0215224 A1 | 8/2012 | Songer |
| 2012/0226321 A1 | 9/2012 | Gonzalez-Hernandez |
| 2012/0303065 A1 | 11/2012 | Larroque-Lahitette |
| 2013/0167334 A1 | 7/2013 | Gephart |
| 2013/0289564 A1 | 10/2013 | Bernstein |
| 2013/0331897 A1 | 12/2013 | Holt |
| 2014/0058445 A1 | 2/2014 | Mattchen |
| 2014/0088688 A1 | 3/2014 | Lilburn |
| 2014/0142638 A1* | 5/2014 | Goodwin ............ A61B 17/842 606/281 |
| 2015/0127003 A1 | 5/2015 | Songer |
| 2015/0182674 A1 | 7/2015 | Schaffer |
| 2015/0342654 A1 | 12/2015 | Gephart |
| 2016/0174997 A1 | 6/2016 | Spitznagel |
| 2016/0331431 A1 | 11/2016 | Gephart |
| 2017/0071648 A1 | 3/2017 | Dell'Oca |
| 2017/0143394 A1 | 5/2017 | Goodwin |
| 2017/0209190 A1 | 7/2017 | Goodwin, Jr. |

FOREIGN PATENT DOCUMENTS

| | | |
|---|---|---|
| WO | 0149191 | 7/2001 |
| WO | 200149191 | 7/2001 |
| WO | 0234120 | 5/2002 |
| WO | 2006088452 | 8/2006 |
| WO | 2011041624 | 4/2011 |
| WO | 2011116364 | 9/2011 |
| WO | 2013003719 | 1/2013 |
| WO | 2014140100 | 9/2014 |
| WO | 2017127692 | 7/2017 |

OTHER PUBLICATIONS

U.S. Appl. No. 62/286,062, filed Jan. 22, 2016, Robert A. Mitchell.
U.S. Appl. No. 62/368,753, filed Jul. 29, 2016, Matthew P. Gephart.

(56) References Cited

OTHER PUBLICATIONS

Acute Innovation-Quick and Easy Installation & Re-entry, Acute Innovation, LLC, htto://www.acuteinnovations.com/oroducts/AcuTie/Installtion, May 16, 2012, 7 pages.
Ease of Wire with the Stability of a Plate, AcuTie Sternal Closure System, Oct. 2010, 12 pages.
Re-Entry Options, AcuTie Sternal Closure System, accessed May 16, 2012, 1 page.
Sternalock Blu Primary Closure System, Biomet Microfixation, Form No. BMF00-3265, Rev 05k1110, 2011, 10 pages.
Technique Guide, Modular Sternal Cable System Flexibility and Strength in Sternal Closure and Repair, Synthes CMF, Jul. 2008, 39 pages.
Technique Guide, Titanium Sternal Fixation System for Stable Internal Fixation of the Sternum, Synthes, Inc., Oct. 2010, 36 pages.

\* cited by examiner

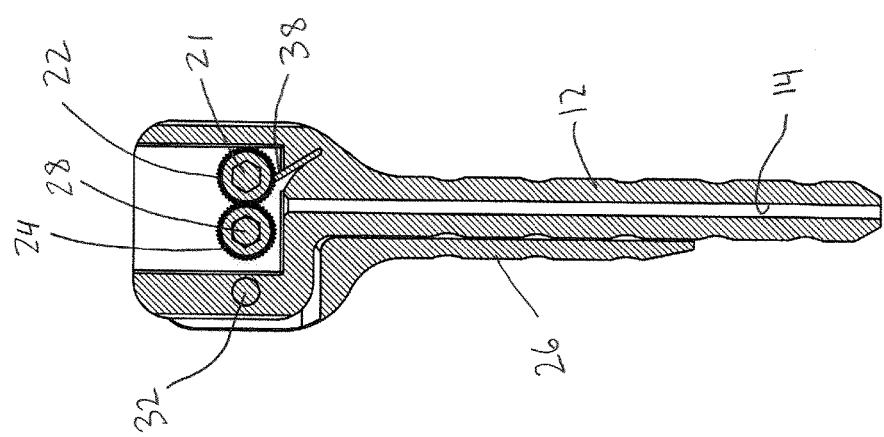

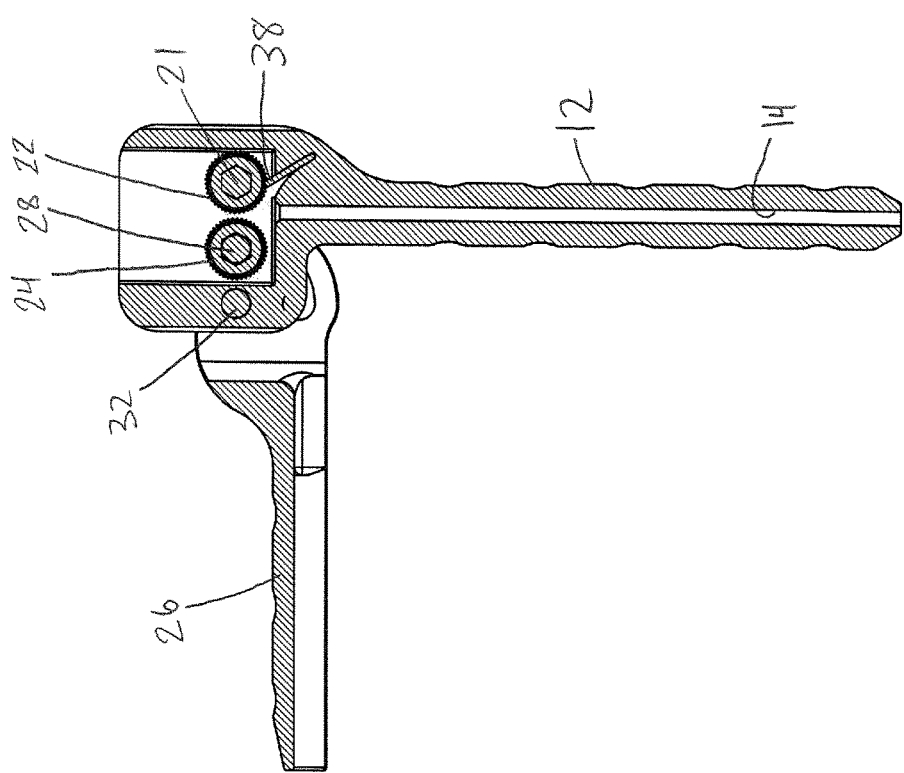

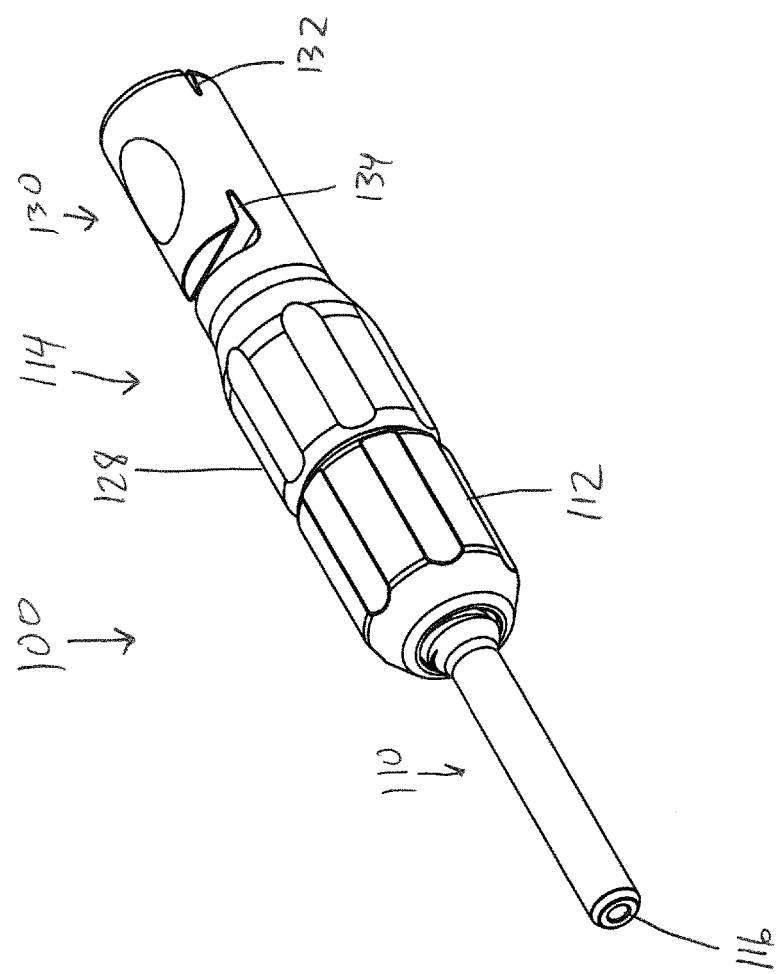

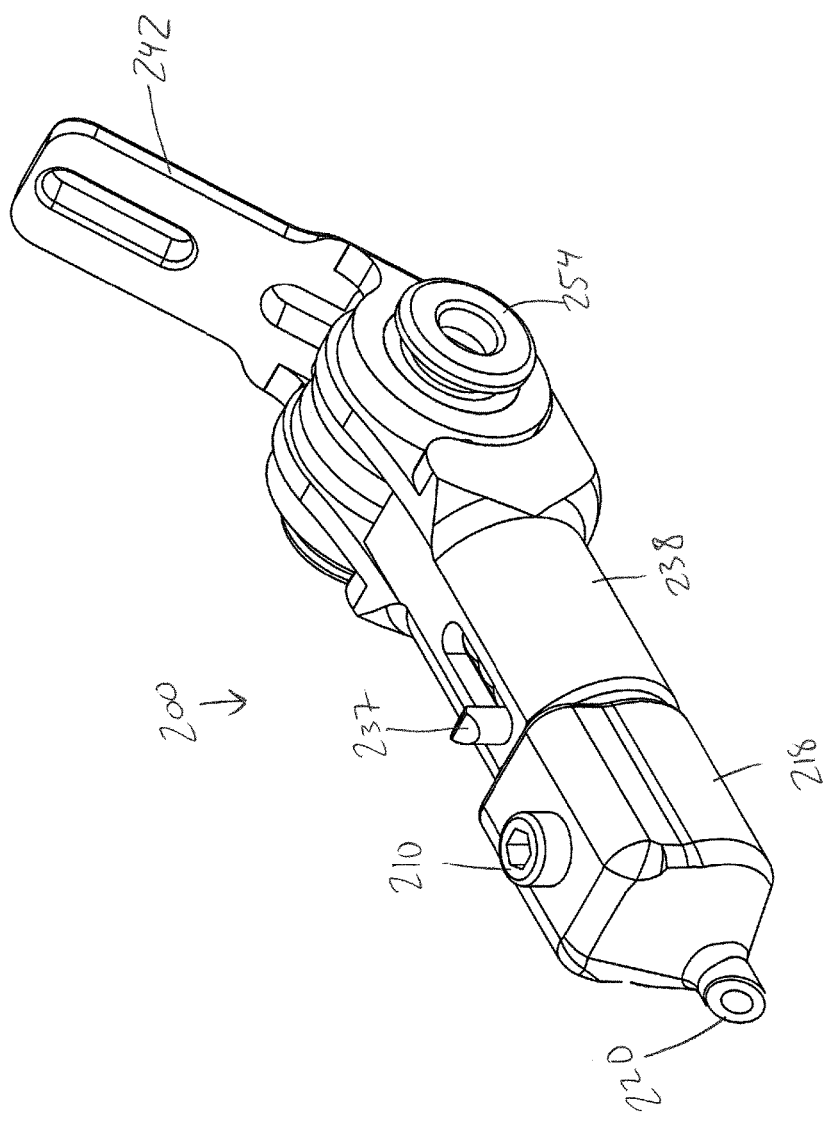

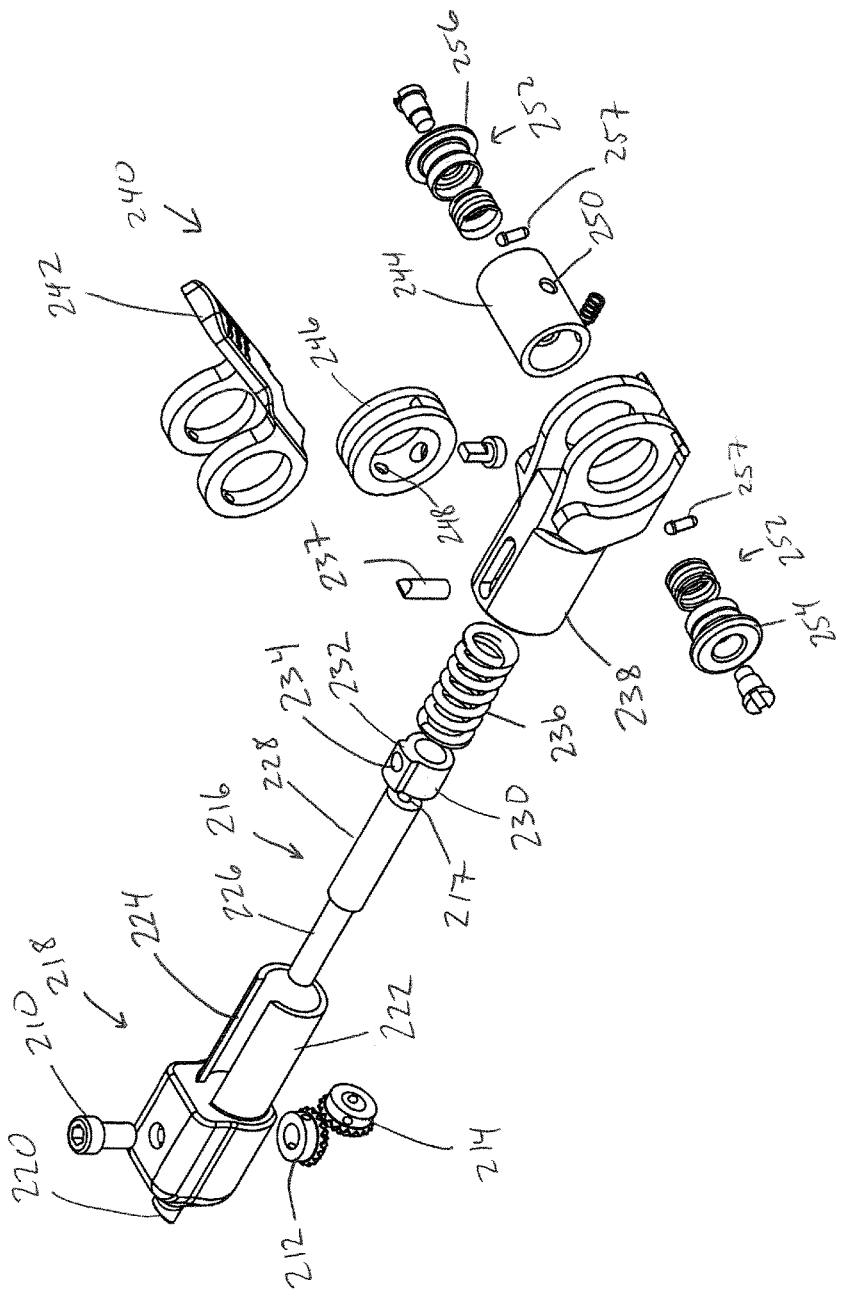

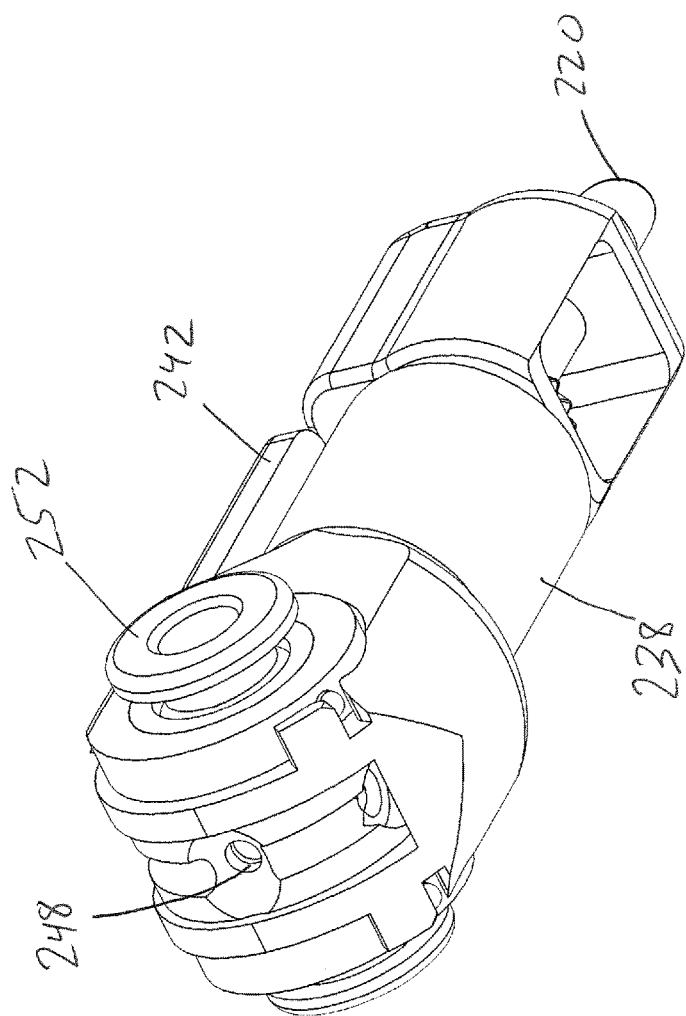

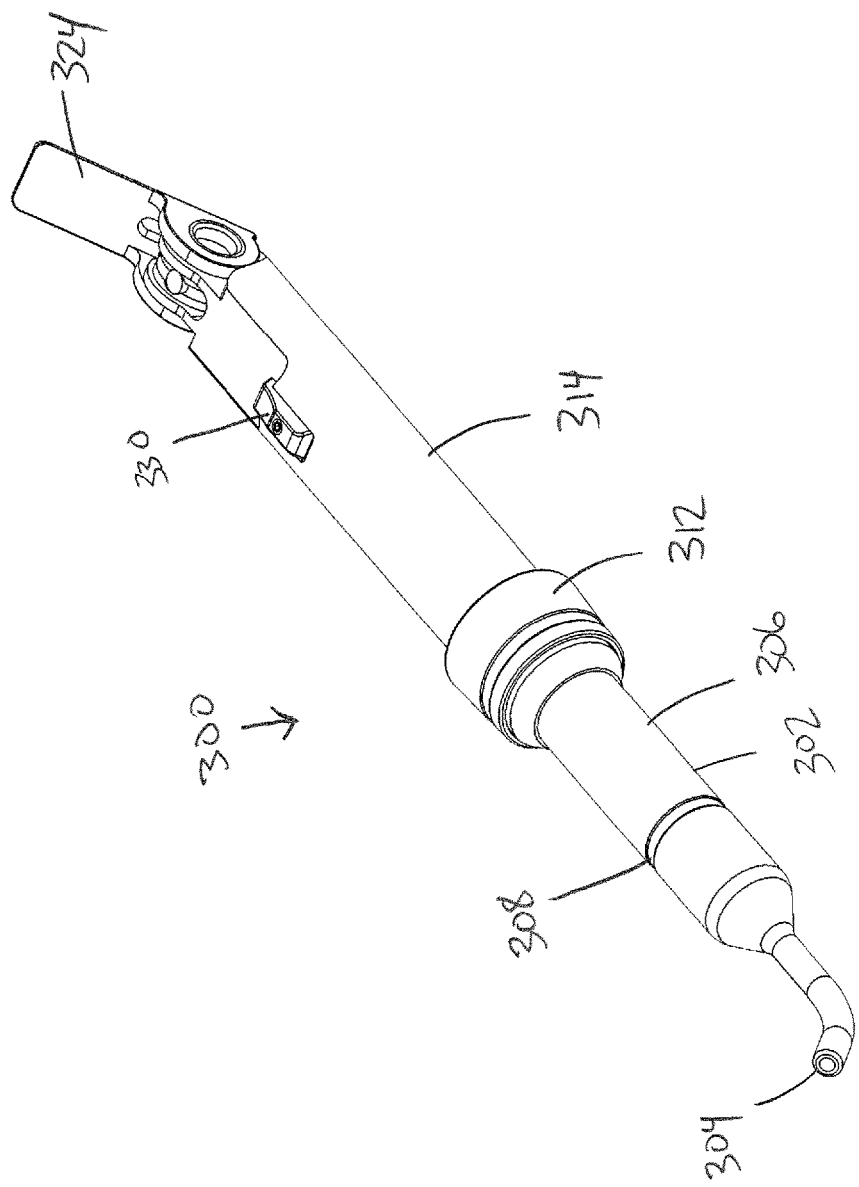

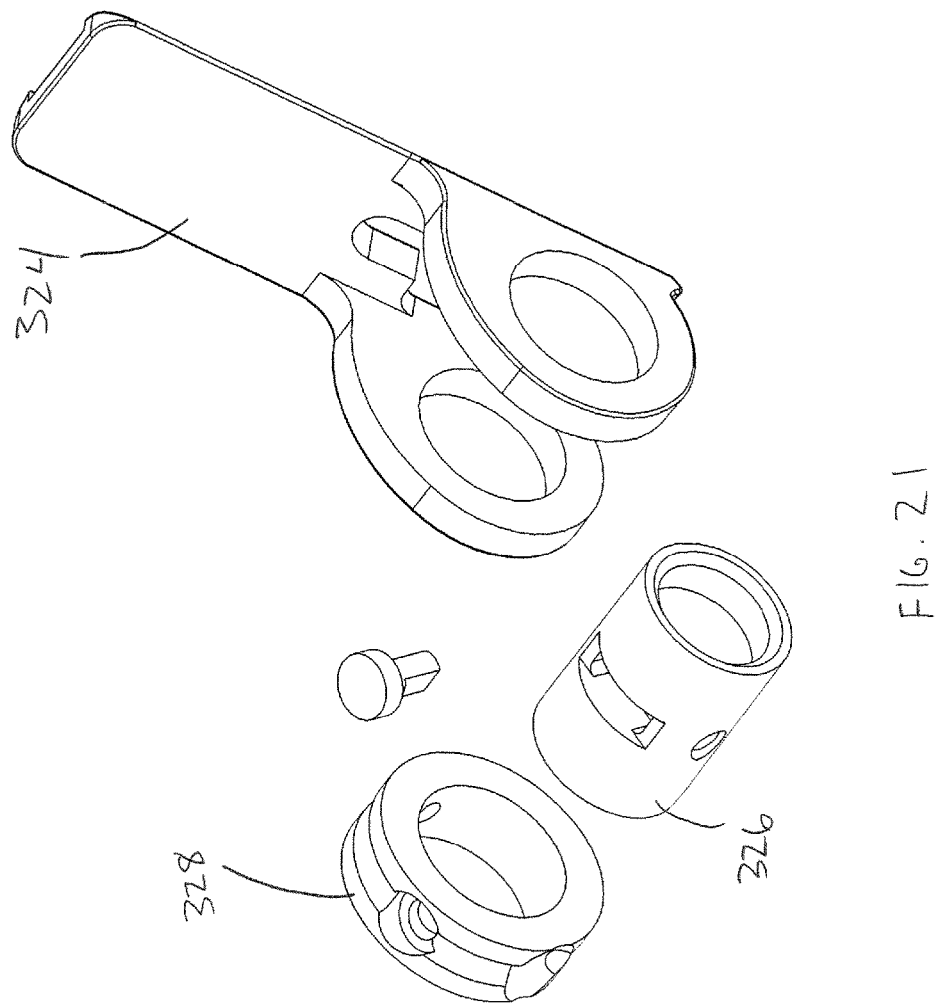

TENSIONING INSTRUMENTS

CROSS-REFERENCE TO RELATED APPLICATION

The application claims the benefit of U.S. Patent Application No. 62/004,022 filed May 28, 2014, which is hereby incorporated by reference in its entirety.

FIELD OF THE INVENTION

The present invention relates generally to apparatuses for tensioning securing devices and, more specifically, to apparatuses for tensioning securing devices in a variety of medical procedures

BACKGROUND

Securing devices, such as cables or wires, are often used in orthopedic surgery for securing bones in place and for fastening implants, such as plates, to the bones. In one type of procedure, a cable having a pair of opposite ends is positioned around one or more bones. The cable has a connector at one end, and the other end is inserted into the connector to form a loop of the cable around the bone or bones. As used herein, the term bone may refer to a bone, a bone fragment, or a portion of a bone. The term cable may refer to metal and non-metal cables, wires, or other elongate securing devices that are configured to be tensioned by a tensioning instrument.

A tensioning instrument may be used to apply tension to the cable and constrict the loop of cable about the bone or bones and an implant, such as a bone plate. Tensioning instruments may be very complex and include, for example, a cable locking mechanism, a cable tensioning mechanism, a detachable re-tension mechanism, and a tension scale. Some prior tensioning instruments use different mechanisms to provide each of these features, which increases the cost and size of the tensioning instrument.

Some surgeries require multiple cables to be implanted that each require tensioning. One prior tensioning instrument that may be used in such a surgery is a pistol-type tensioner having a detachable tip for holding tension in each surgical cable. During surgery, the tensioning instrument is used to apply a desired amount of tension to a first cable, the tip is engaged to the cable to hold tension in the cable construct, the tip is detached, a new tip is connected to the tensioning instrument, and the tensioning instrument is moved to the next cable. This procedure is repeated until all of the cables have been tensioned. Connectors on the cables are then crimped to secure the cables on the bones. One problem with this approach is that once a cable has been tensioned and the tensioning instrument detached from the tip, the tension in the cable may change, for example, due to tensioning of another cable around nearby bones. In that case, re-tensioning of the cable would be necessary. However, the operator would not be aware of the change in tension unless the tensioning instrument is re-connected to the first tip and used to gauge the tension in the first surgical cable.

Some known tensioning instruments have numerous components, are relatively large, and are quite complex. These instruments are designed to be reused, due to their relatively high cost and complexity. However, complex instruments are often difficult to clean properly after use, often requiring a skilled technician to disassemble the instrument and clean individual parts before reassembling. Accordingly, complex tensioning instruments are relatively expensive and are associated with ongoing cleaning expenses with each use.

SUMMARY

In accordance with one aspect of the present invention, a tensioning instrument is provided that enables a user to quickly and easily apply a desired amount of tension to a securing device such as a surgical cable. In numerous forms, the tensioning instrument is configured with a minimal number of parts for ease of manufacture and use, and also for reducing costs to permit single use applications, eliminating the need for cleaning of the instrument for reuse. In some forms, the tensioning instrument is configured to maintain the selected amount of tension while other cables are tensioned, eliminating the need for retensioning the cable that has already been tensioned.

In one form, a cable-tensioning instrument includes a distal shaft member defining a first cable passageway portion that extends through the distal shaft member about a longitudinal axis for receiving a cable. A proximal locking member defines a second cable passageway portion that extends therethrough aligned with the longitudinal axis and terminates at a proximal end of the proximal locking member. The proximal locking member includes a cable anchoring portion for fixing the cable thereto. A rotatable actuator is disposed about the distal shaft member for shifting the distal shaft member with respect to the proximal locking member along the longitudinal axis to tension a cable that extends through the first and second cable passageway portions and is fixed to the cable anchoring portion. In one form, the cable anchoring portion includes a cleat portion spaced from the proximal end of the proximal locking member for receiving a portion of the cable thereabout for fixing the cable to the proximal locking member. The cable anchoring portion may include a groove at the proximal end of the proximal locking member that is oriented transversely with respect to the longitudinal axis and that is in communication with the second cable passageway for receiving a cable extending from the second cable passageway for guiding the cable at least partially toward the cleat portion, such that the cable may be wrapped at least partially around the cable anchoring portion to secure the cable to the proximal locking member. The cleat portion and the transversely oriented groove may each have a v-shaped terminal portion for capturing the cable therein via an interference fit to encourage secure fixation of the cable to the proximal locking member. The cleat portion in one form opens distally to allow the cable extending from the second passageway at the proximal end of the proximal locking member to be wrapped around the proximal locking portion between the groove at the proximal end and the cleat portion.

The distal shaft member may include a threaded portion for engaging with a mating threaded portion of the rotatable actuator such that rotation of the rotatable actuator shifts the proximal locking member linearly along the longitudinal axis. The distal shaft member may also include an indexing portion for inhibiting rotation of the distal shaft member with respect to the proximal locking member when the rotatable actuator is rotated with respect to the distal shaft member. For example, the proximal locking member includes an interior cavity having a non-cylindrical configuration, such as a generally rectangular shape, and the indexing portion has a corresponding non-cylindrical configuration for engaging with the interior cavity to inhibit rotation of the distal shaft member with respect to the proximal locking member. In some forms, the proximal locking member includes a cylindrical surface portion about which the rotatable actuator is rotatably mounted.

In another form, a cable-tensioning instrument includes a body including a distal tip defining an opening for receiving a cable. A passageway extends along a longitudinal axis from the distal tip opening to a proximal end opening for receiving a cable to be tensioned therethrough. A rotatable drive shaft is disposed within the instrument body and an actuator is connected to the drive shaft for rotating the drive shaft. A traveler member disposed about the drive shaft and configured to shift therealong when the drive shaft is rotated by the actuator. A locking mechanism is configured to fix a cable thereto and is operably engaged with the traveler member to be shifted along the longitudinal axis by the traveler member. In particular, the traveler member biases the locking mechanism away from the distal tip of the instrument body to tension the cable fixed to the locking mechanism when the actuator is actuated by a user. Advantageously, the instrument may be sized and configured to fit within a palm of a user's hand, which allows the instrument to be left temporarily in place after tensioning a cable while other cables are tensioned using additional instruments. This way, the tension applied to the cable may remain constant, or if needed to be adjusted, may be done quickly and easily by actuating the actuator.

In one form, a biasing member is operably engaged with the traveler member and the locking mechanism for providing a biasing force operable to urge the locking mechanism proximally away from the distal tip for applying tension to the cable. Optionally, a tension indicator is connected to the traveler member for indicating the amount of tension applied to the cable. The locking mechanism may be provided with a lever with an opening disposed therein for receiving at least a portion of the tension indicator.

The drive shaft may include a threaded portion and the traveler member may have a mating threaded portion for engaging with the threaded portion of the drive shaft to shift the traveler member therealong when the drive shaft is rotated by the actuator. The drive shaft includes a longitudinally-oriented passage that extends through the shaft and forms at least part of the tool passageway for receiving the cable therein.

The instrument body may include a distal member including the distal tip and a proximal portion having a longitudinally oriented slot. The traveler member may include an index portion which engages with the longitudinally oriented slot to inhibit rotation of the traveler member when the drive shaft is rotated so that the traveler member translates along a length of the drive shaft when the drive shaft is rotated. Further, the instrument body may also have a proximal member which includes the locking mechanism, and the proximal portion of the distal member can include a smooth outer surface for being received in and slidingly engaged with a corresponding interior portion of the proximal member such that the proximal and distal members are configured to shift with respect to one another along the longitudinal axis to apply tension to the cable.

The actuator may take the form of a rotary member having a drive head for engaging with a mating tool for rotating the rotary member. The rotary member is operably connected to the distal member and the drive shaft for rotating the drive shaft via a corresponding rotation of the rotary member. In one form, a drive gear connected to the rotary member and a mating driven gear connected to the drive shaft are in operable engagement such that rotation of the rotary member causes a corresponding rotation of the gears and the drive shaft.

In some forms, the tensioning instrument has a pretensioning mechanism that allows a predetermined preload tension to be applied to the cable. The pretensioning mechanism is adjusted to set a desired preload before the tensioning instrument is connected to the surgical cable. Once the pretensioning mechanism is set at the desired preload, the cable is attached to the instrument and the operator simply actuates a release to apply the preload of the pretensioning mechanism to the cable. In some forms a coil spring may be used to pretension the tensioning mechanism, and in other forms, the instrument itself is effectively a resilient biasing mechanism that relies on its resiliency to tension the cable. As discussed in greater detail below, this functionality allows a user to configure a plurality of tensioning instruments to provide a common amount of tension to a plurality of surgical cables and allows for quick and simple operation.

BRIEF DESCRIPTION OF THE DRAWINGS

FIG. 6B is a cross-sectional view of the tensioning instrument of FIG. 1 with the tensioning mechanism in the locked configuration;

FIG. 6C is a cross-sectional view of the tensioning instrument of FIG. 1 with the tensioning mechanism in the released configuration;

FIG. 7 is a perspective view of an alternate tensioning instrument in accordance with the present invention;

FIG. 12B is a perspective view of the instrument of FIG. 12A in the load or release configuration;

FIG. 13 is an exploded perspective view of the tensioning instrument of FIG. 12A;

FIG. 14 is a proximal perspective view of the tensioning instrument of FIG. 12A;

FIG. 18 is a perspective view of an alternate tensioning instrument in accordance with the present invention;

FIG. 21 is an exploded perspective view of components of the locking mechanism of the tensioning instrument of FIG. 18;

FIG. 25 is a perspective view of the tensioning instrument of FIG. 23 in the compressed configuration.

DETAILED DESCRIPTION

Figure 1:
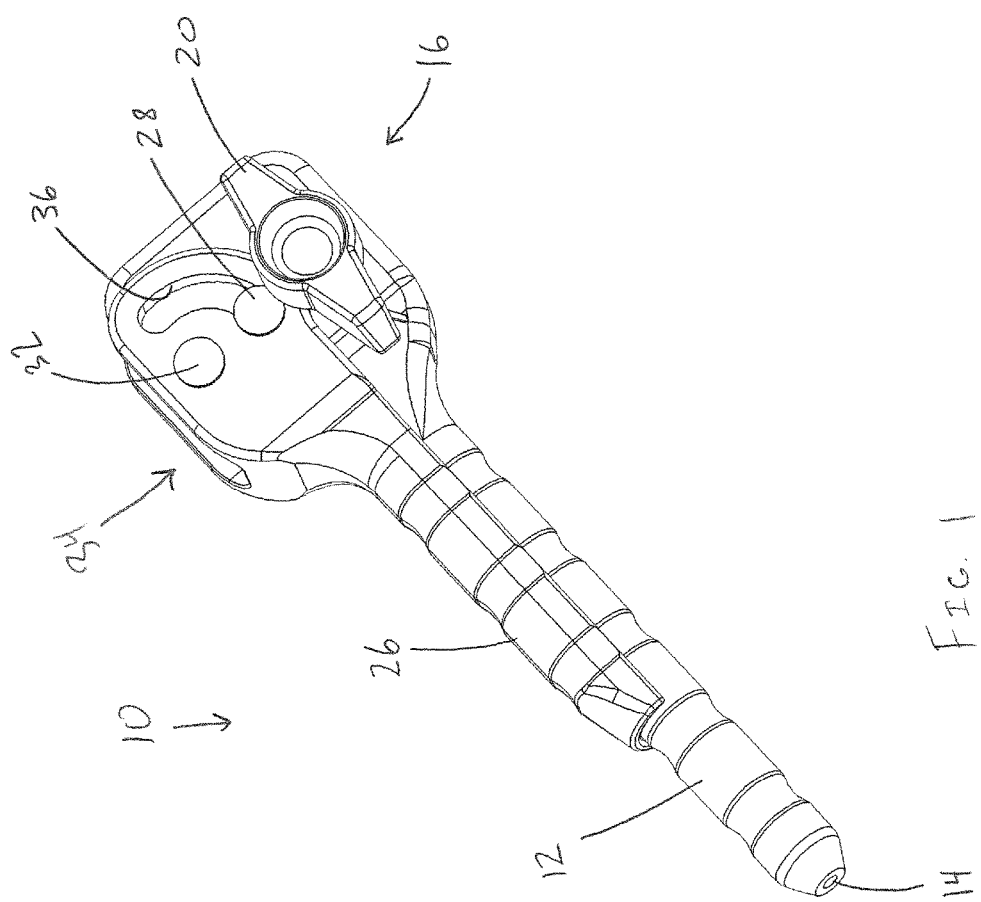
FIG. 1 is a perspective view of a tensioning instrument in accordance with the present invention.
Figure 2:
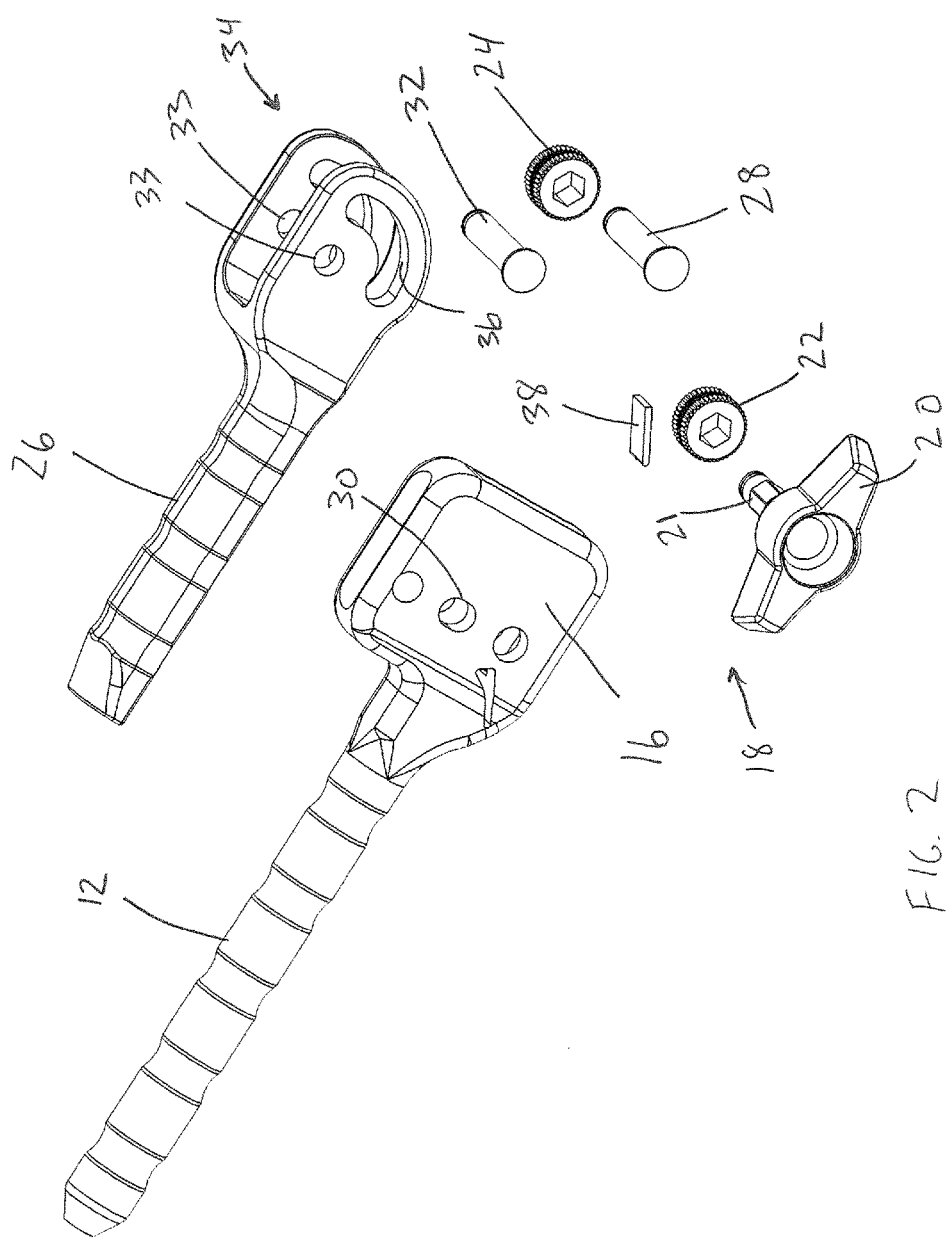
FIG. 2 is an exploded perspective view of the tensioning instrument of FIG. 1.
Figure 3:
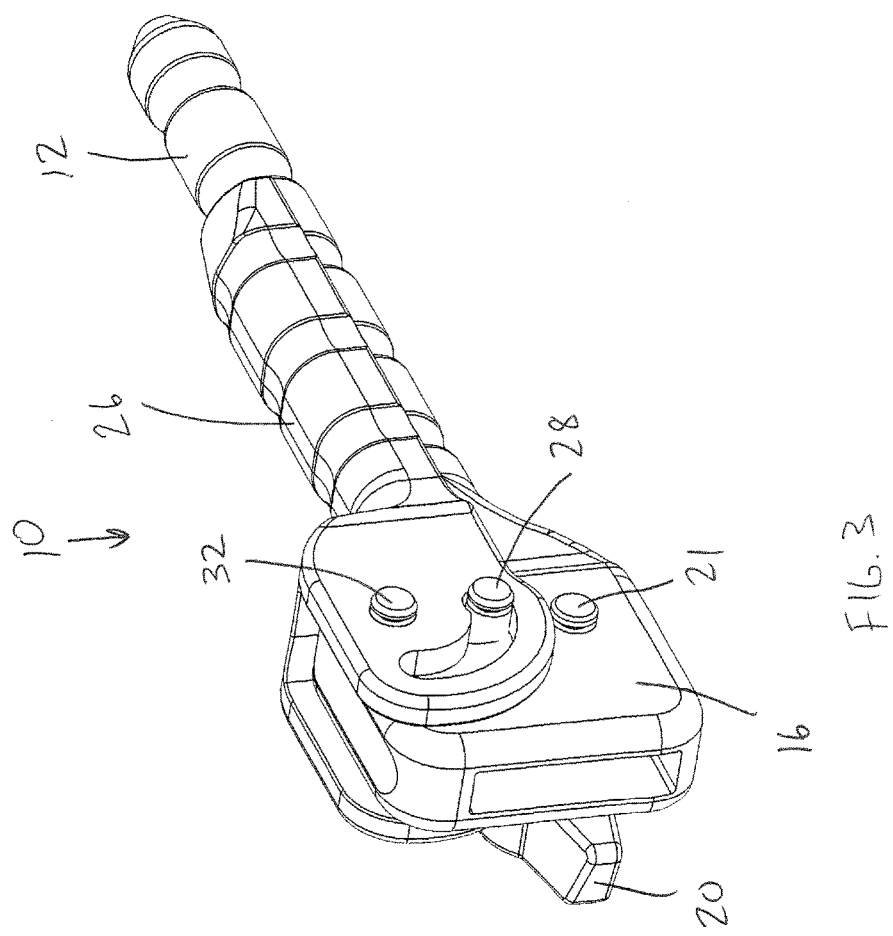
FIG. 3 is a perspective view of the tensioning instrument of FIG. 1.
Figure 4:
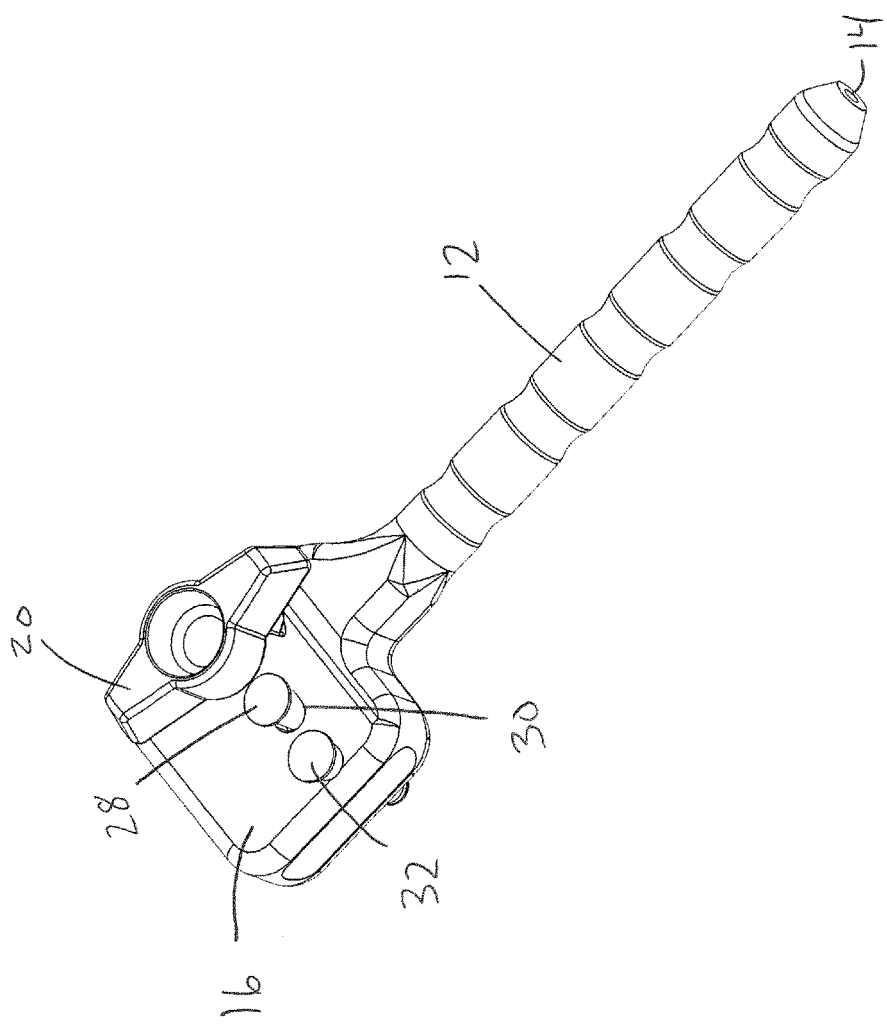
FIG. 4 is a perspective view of the tensioning instrument of FIG. 1.
Figure 5:
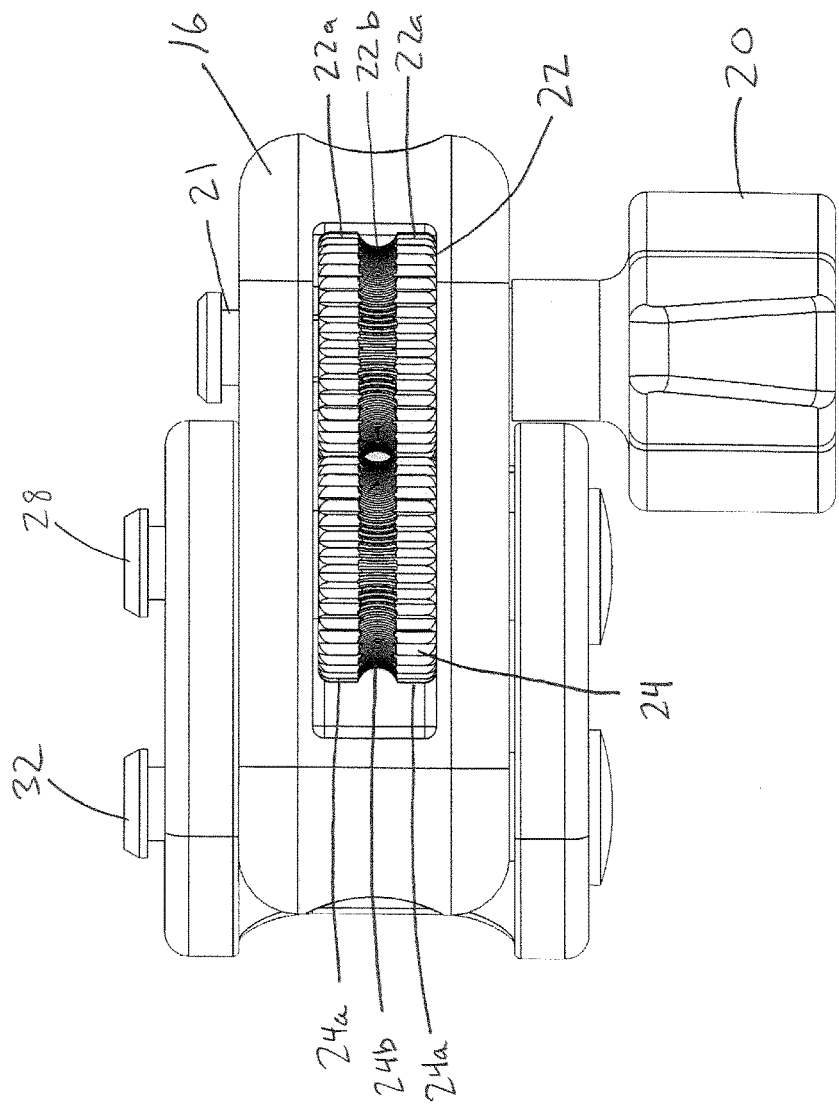
FIG. 5 is a proximal end view of the tensioning instrument of FIG. 1.

With reference to FIGS. 1 and 2, a tensioning instrument 10 is provided for tensioning a securing device, such as a cerclage cable about a bone. The cerclage cable construct may include a cable and a cerclage connector disposed at one end of the cable for locking the cerclage cable about the bone. The instrument 10 includes a body with a shaft portion 12 which defines a longitudinal passageway 14 that extends into the head portion 16 of the body. A tensioning mechanism 18 is connected to the head portion 16 and includes an actuator, such as a knob 20, which is rotated to turn a pair of geared wheels 22, 24 between which the cable is threaded. As shown in FIG. 5, the wheels 22, 24 are configured with toothed perimeter portions 22a, 24a which mesh with each other to transmit torque from the knob 20 from drive wheel 22 to driven wheel 24. Between the toothed perimeter portions 22a, 24a is a central recessed cable gripping portion 22b, 24b, which is configured with a plurality of ridges or teeth for gripping a cable located between the gripping portions 22b, 24b of each wheel 22, 24. Drive wheel 22 is mounted on a shaft portion 21 which is connected to knob 20 and is driven thereby. The tensioning mechanism also includes a spring member 38 which acts as a pawl or ratchet and engages with the drive wheel 22 to keep the wheels 22, 24 from derotating, i.e., turning in a direction (counterclockwise and clockwise, respectively) that would allow the cable to unwind and lose tension or be released from between the wheels 22, 24.

Figure 6A:
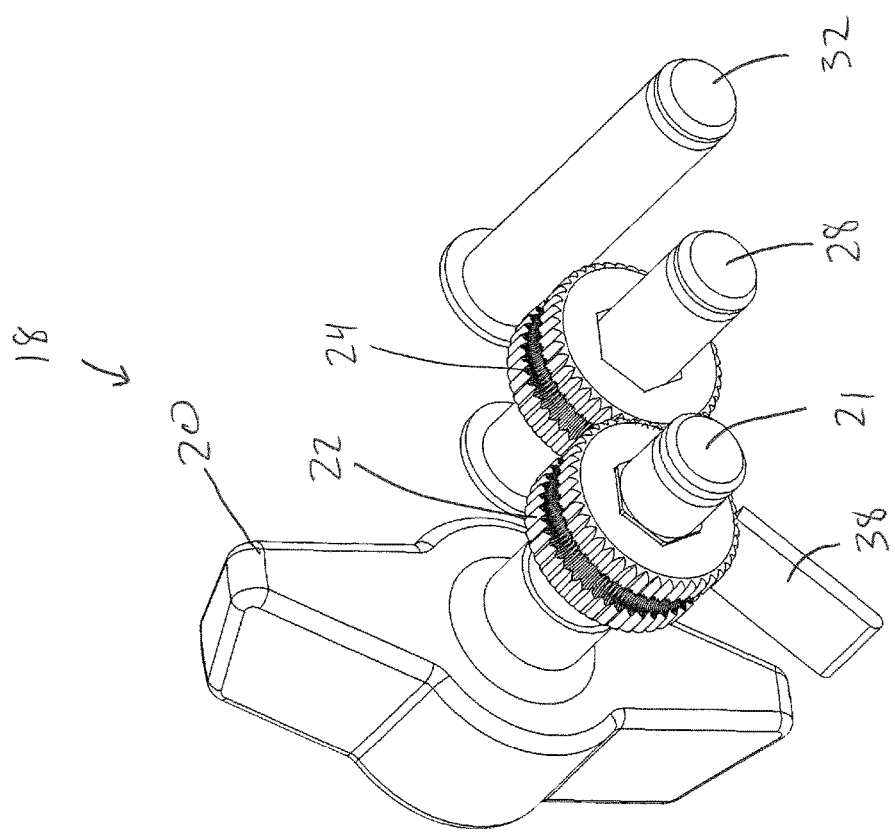
FIG. 6A is perspective view of components of the tensioning mechanism of the tensioning instrument of FIG. 1.

The instrument 10 includes a release mechanism in the form of a release lever 26, which is operably connected to driven wheel 24 via movable pin 28. The movable pin 28 is located within an elongate groove 30 in the head portion 16, which allows the pin 28 and driven wheel 24 to translate away from the wheel 22 to allow the cable to be released from between the two wheels. The release lever 26 is pivotally connected to the head portion 16 via a pin 32 which extends through a pair of openings 33 in the proximal end portion 34 of the lever. A pair of arcuate grooves 36 are located in the proximal end portion 34 of the release lever 26 in which the pin 28 is movably captured. The grooves 36 are configured to move the pin 28 and driven wheel 24 away from the drive wheel 22. In particular, the grooves 36 have a radius that changes slightly such that as the release lever 26 is pivoted away from the shaft portion 12, the groove urges the pin 28 toward the pin 32. Because pin 28 is captured in elongate groove 30, the pin is permitted to shift. FIGS. 6B and 6C show the release lever 26 in the closed and released positions, respectively. The movement of the driven wheel 24 is shown in FIG. 6C, which corresponds to the release configuration of the tensioning mechanism.

In operation, the release lever 26 is opened to move the driven wheel 24 away from the drive wheel 22 to allow a cable to be threaded through the passageway 14 and between the wheels. With the distal end of the shaft portion 12 abutted with the cable connector, the release lever 26 is then closed to lock the cable between the wheels 22, 24 in the gripping portions 22b, 24b thereof. The knob 20 is then rotated in a clockwise direction by the user to tension the cable. Once the desired tension is reached, the user will crimp or lock the cable connector and can then remove the instrument by once more opening the release lever 26. The loose cable end can then be removed from the instrument 10.

Although this embodiment and some of the following embodiments are shown without a scale for displaying tension, one could be added as would be apparent to one of skill in the art. The body of the instrument 10 may be preferably made of a plastic, and in view of the few number of parts and use of affordable materials, may lend itself to be a single-use device, eliminating the need for cleaning after use.

Figure 8:
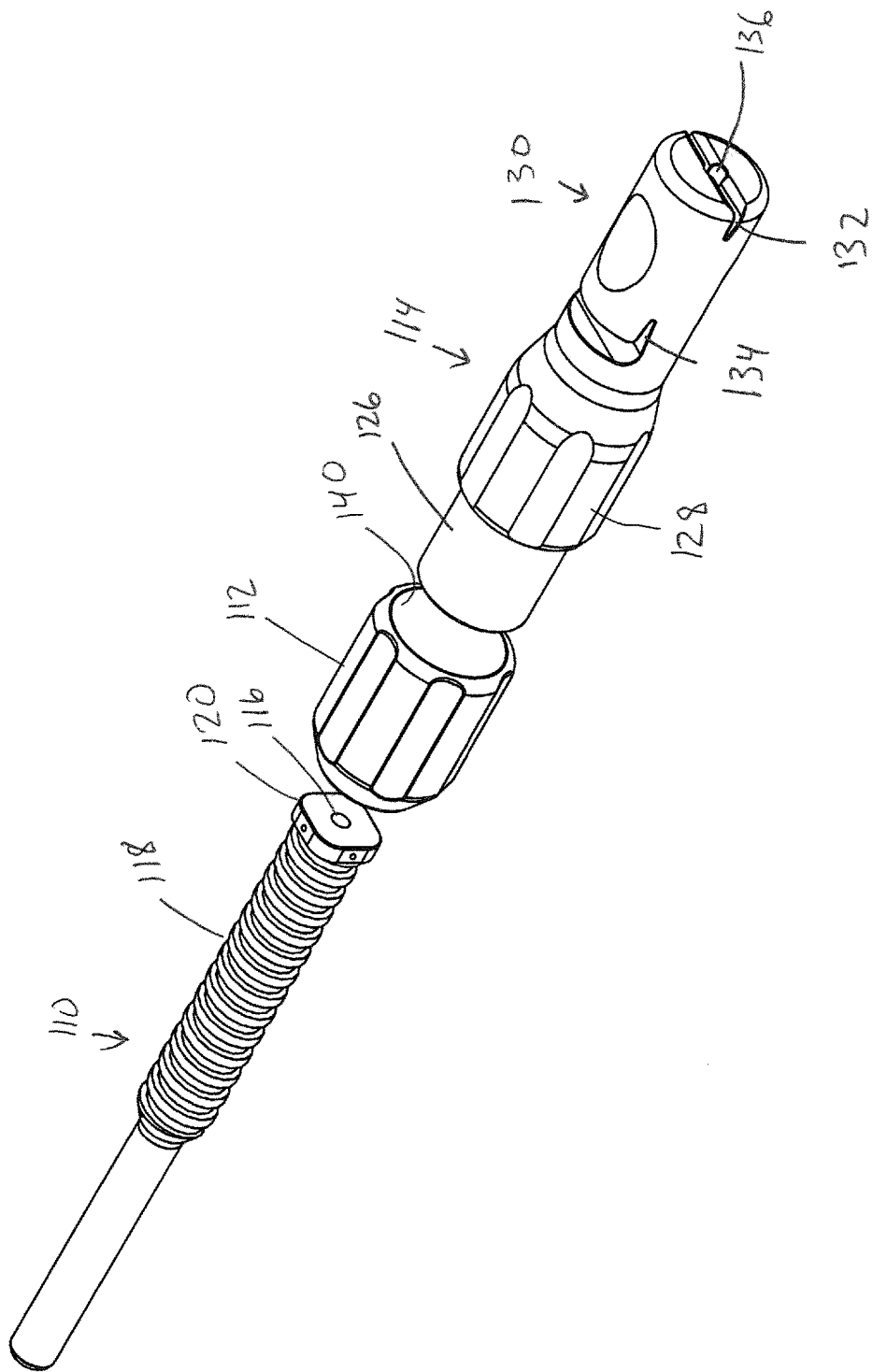
FIG. 8 is an exploded perspective view of the tensioning instrument of FIG. 7.
Figure 9:
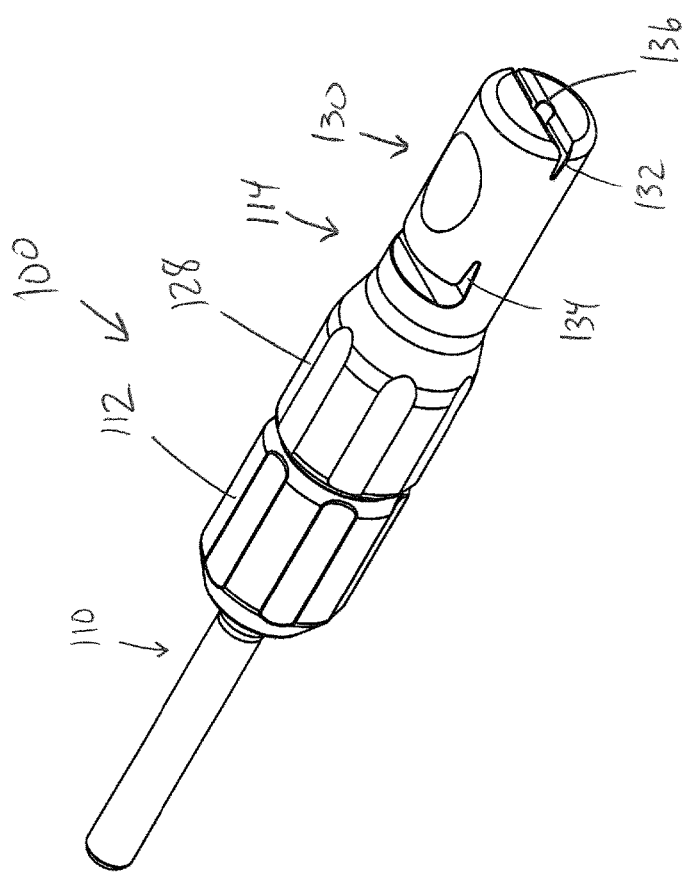
FIG. 9 is a perspective view of the tensioning instrument of FIG. 7.
Figure 10:
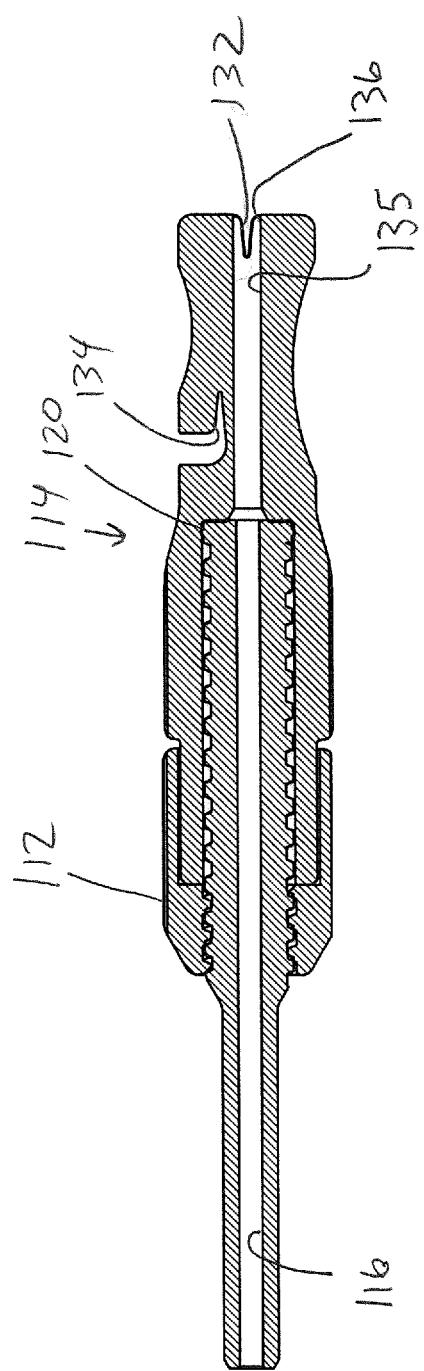
FIG. 10 is a side cross-sectional view of the tensioning instrument of FIG. 7 taken along the superior-inferior plane along the longitudinal instrument axis.
Figure 11:
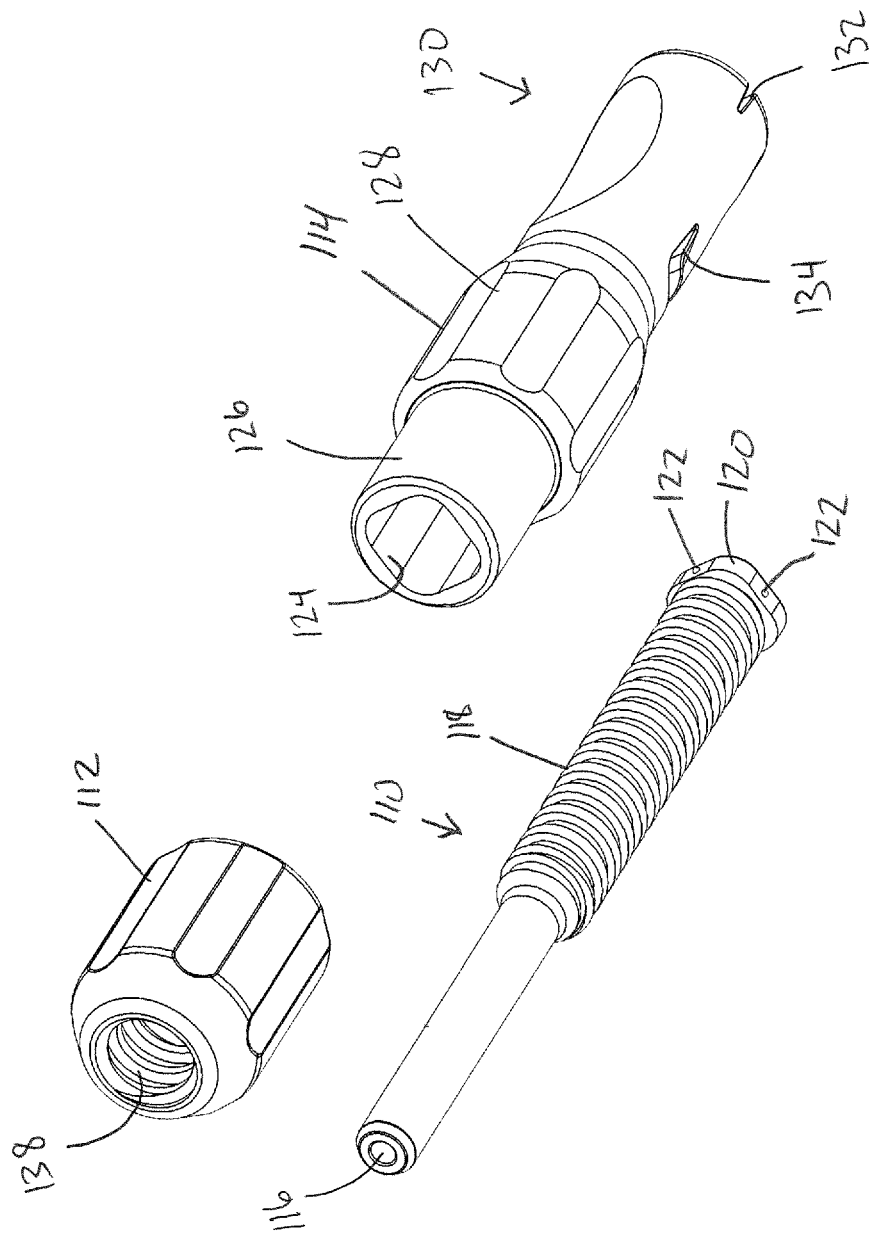
FIG. 11 is an exploded perspective view of the instrument of FIG. 7.

Another tensioning instrument in accordance with the present invention is disclosed in FIGS. 7-11. As shown in FIGS. 8 and 11, the instrument 100 includes a distal shaft member 110, an actuator in the form of a rotatable barrel 112, and a proximal locking member 114. The distal shaft member 110 includes a distal end for engaging with a cable connector, a first passageway portion 116 that extends through the distal shaft member along the longitudinal axis of the shaft, and a proximal threaded portion 118. At the proximal end of the distal shaft member 110 is an indexing feature having a non-cylindrical configuration, i.e., in the form of a square-like protrusion 120 which includes rollers 122 for engaging with a complimentary shaped interior cavity 124 of the proximal locking member 114, which prevents the distal shaft member 110 from rotating with respect to the proximal locking member 114, but allows the proximal locking member 114 to translate with respect to the distal shaft member 110, i.e., longitudinally along the tool axis.

The proximal locking member 114 includes a distal end portion 126 for engaging with the barrel actuator 112, a grip portion 128, a second passageway portion 135 that extends through the proximal locking member aligned with the longitudinal tool axis, and a proximal cable anchoring portion 130. The cable anchoring portion 130 is advantageously configured to securely fix poly cable. For example, the cable anchoring portion 130 includes a pair of opposed recesses or cleat portions 132, 134 which together function as a cleat for wrapping the cable thereabout and have terminal portions having a v-configuration for capturing the cable therein via a friction or interference fit. The cleat portion 134 is spaced from the proximal end of the cable anchoring portion 130, and the v-shaped portion of the cleat portion opens distally for securely fixing the cable therein. As shown in FIG. 8, the proximal end of the proximal locking member 114 includes an opening 136 disposed in the transversely oriented groove or recess 132 so that the cable may pass through the proximal locking member and then be wrapped about the proximal cable anchoring portion 130 between the groove 132 and cleat portion 134 to lock the cable in place.

As shown in FIG. 11, the rotatable barrel actuator 112 has a generally cylindrical configuration with a throughopening including a distal threaded portion 138 for engaging with the proximal threaded portion 118 of distal shaft member 110, and a proximal smooth cylindrical surface portion 140 for being rotatably mounted on the distal end portion 126 of the proximal locking member 114.

In operation, the cable is threaded through the first passageway portion 116 at the distal end of the distal shaft member 110, and the second passageway portion 135, exiting at the proximal opening 136. The free end of the cable is then wound tightly about the proximal cable anchoring portion 130 including the cleat portions 132, 134 to lock the cable in place. Then the barrel actuator 112 is rotated clockwise to advance both the actuator 112 and the proximal locking member 114 proximally with respect to the distal shaft member, which effectively increases the length of the instrument and pulls the cable proximally, thereby tensioning the cable. Once the cable reaches the desired tension, the cable may be clamped and then removed from the instrument by unwrapping the cable from the cable anchoring portion 130.

The body of the instrument 100 may be preferably made of a plastic, and in view of the few number of parts and use of affordable materials, may lend itself to be a single-use device, eliminating the need for cleaning after use.

Figure 12A:
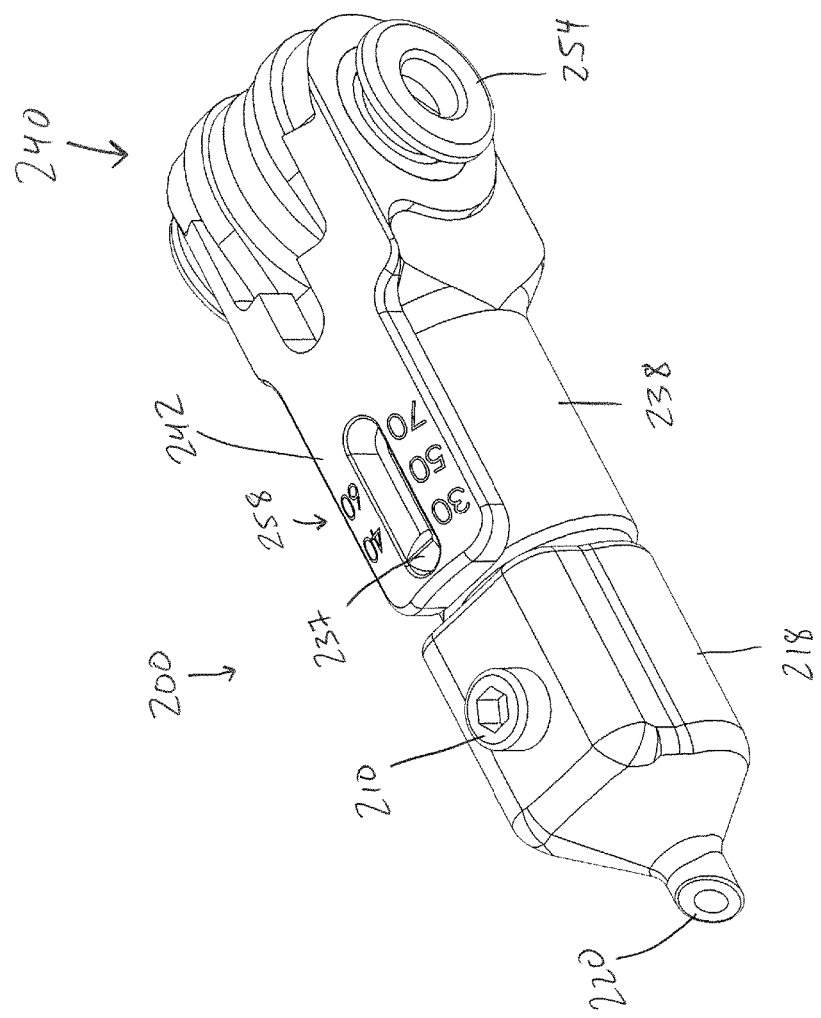
FIG. 12A is a perspective view of an alternate tensioning instrument in the locked orientation in accordance with the present invention.
Figure 15:
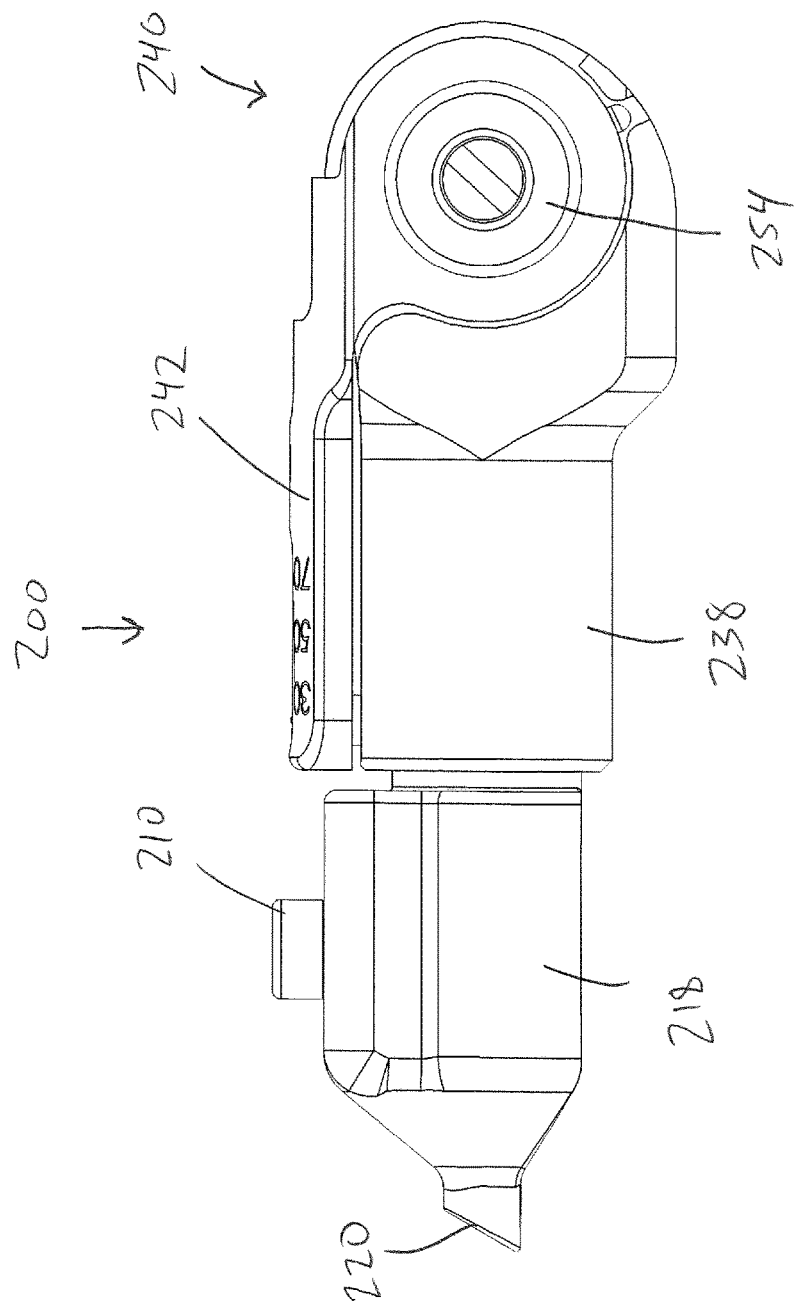
FIG. 15 is side view of the tensioning instrument of FIG. 12A.

Another tensioning instrument in accordance with the present invention is disclosed in FIGS. 12A-17. As shown in FIGS. 12A and 13, the instrument 200 includes a tensioning mechanism including a tensioning screw 210 attached to a drive bevel gear 212 and a driven bevel gear 214 mounted on a drive shaft 216. The tensioning screw 210 and bevel gears 212, 214 are at least partially disposed in a distal housing portion 218, which includes a distal tip 220 and a proximal cylindrical portion 222 which includes indexing slot 224, which extends longitudinally along a superior portion of the proximal cylindrical portion 222.

The drive shaft 216 has a passageway 217 extending therethrough and includes a distal portion 226 and a threaded proximal portion 228, which has a larger diameter than the distal portion 226. A traveler member in the form of annular ring member 230 is threadedly mounted on the threaded proximal portion 228 and includes a keyed portion 232, which is located within indexing slot 224 to keep the annular ring member 230 from rotating when the shaft 216 is rotated by the tensioning screw 210. When the shaft 216 is rotated, the annular ring member 230 is driven proximally on the threaded proximal portion 228 of the shaft, thereby compressing tensioning spring 236 against an interior wall of the proximal housing member 238. The annular ring member 230 also includes a recess 234 for mounting with an indicator 237, which indicates the amount of tension applied to the cable.

The proximal housing member 238 is movably mounted on the proximal cylindrical portion 222 of the distal housing portion 218, such that when the tensioning screw 210 is rotated, the proximal housing member 238 is urged proximally. However, because a cable extends through the body of the instrument 200 and is locked to the locking mechanism 240 at the proximal end of the proximal housing member 218, the cable prevents substantial movement of the proximal housing member 218 once any slack is removed from the cable, and further compression of the spring 236 increases tension on the cable.

Figure 16:
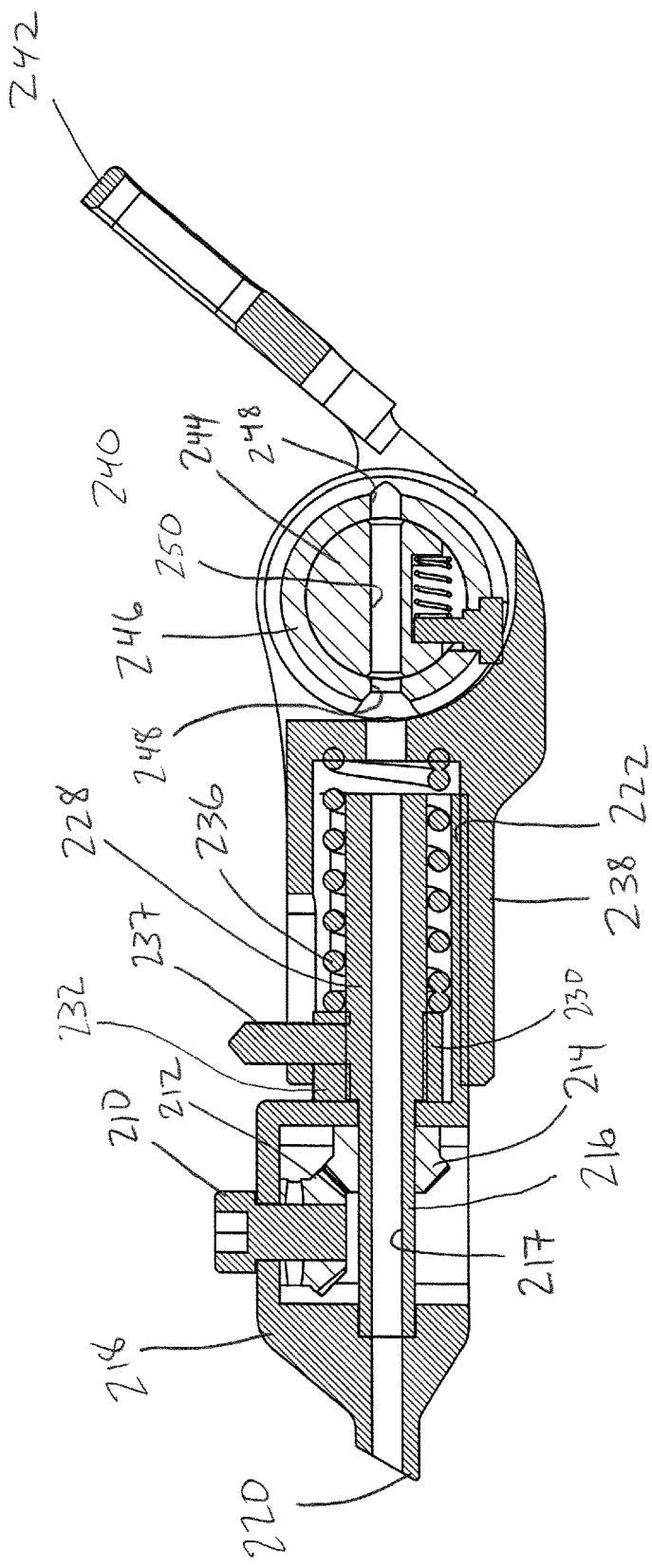
FIG. 16 is a side cross-sectional view of the tensioning instrument of FIG. 12B taken along the superior-inferior plane along the longitudinal instrument axis.
Figure 17:
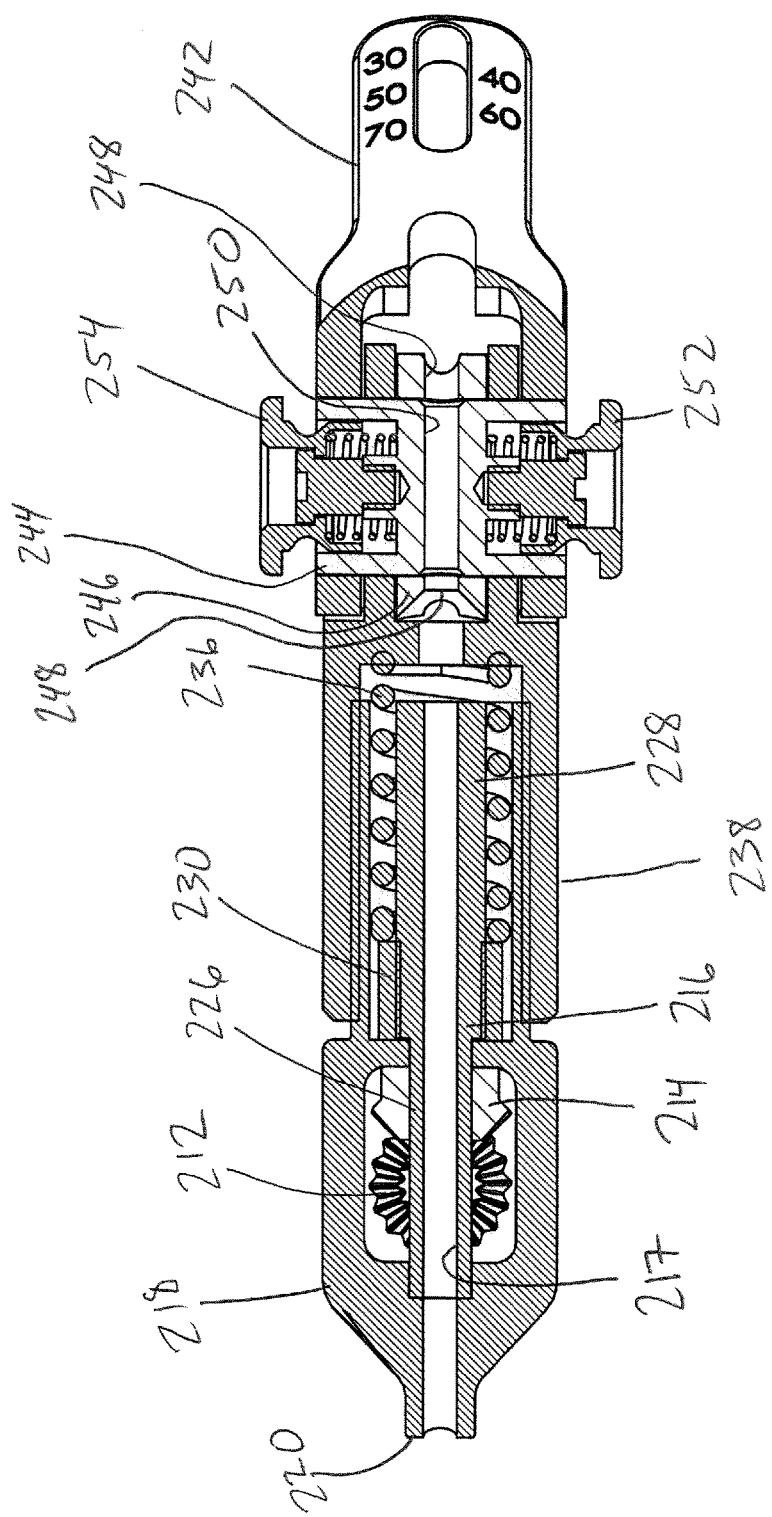
FIG. 17 is a top cross-sectional view of the tensioning instrument of FIG. 12B taken along the transverse plane along the longitudinal instrument axis.
Figure 19A:
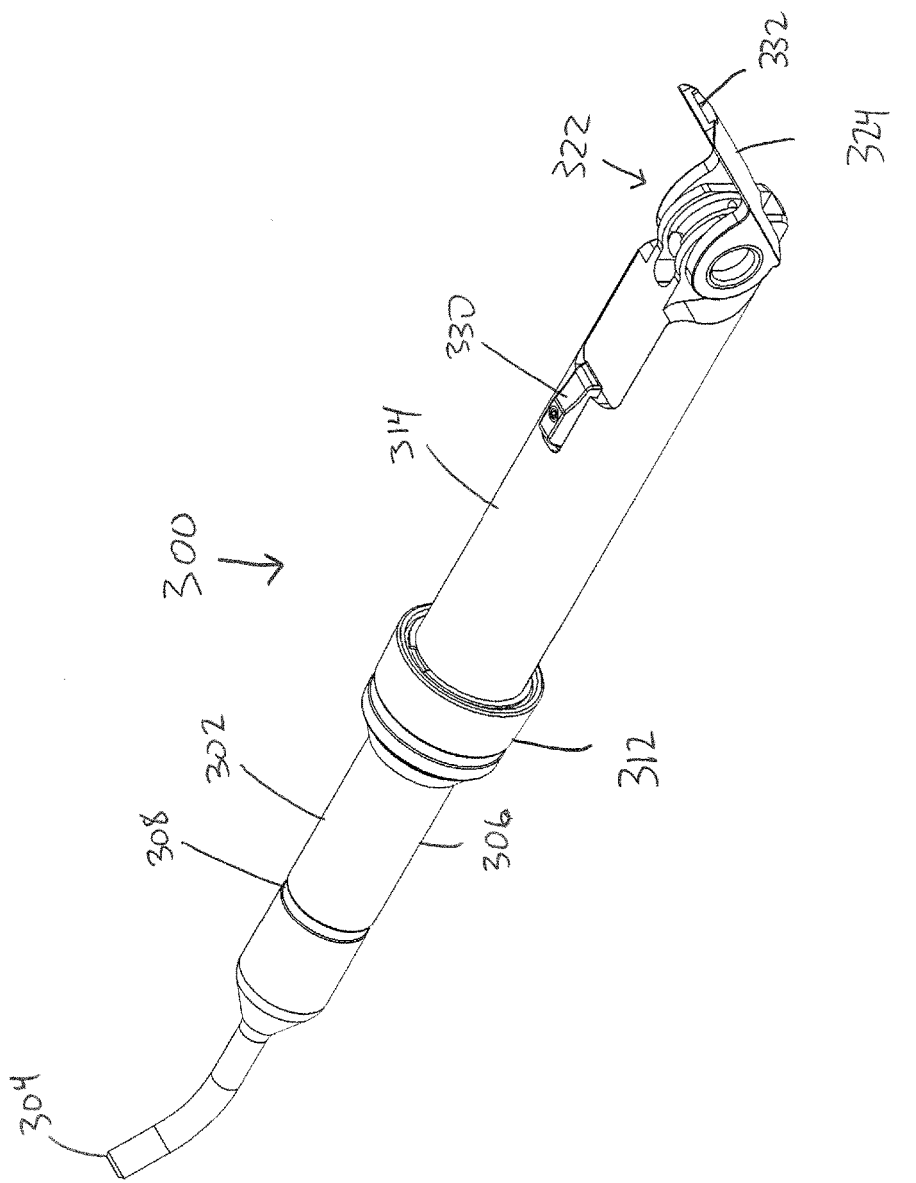
FIG. 19A is a perspective view of the tensioning instrument of FIG. 18 in the unlocked or release configuration and the unloaded configuration.
Figure 19B:
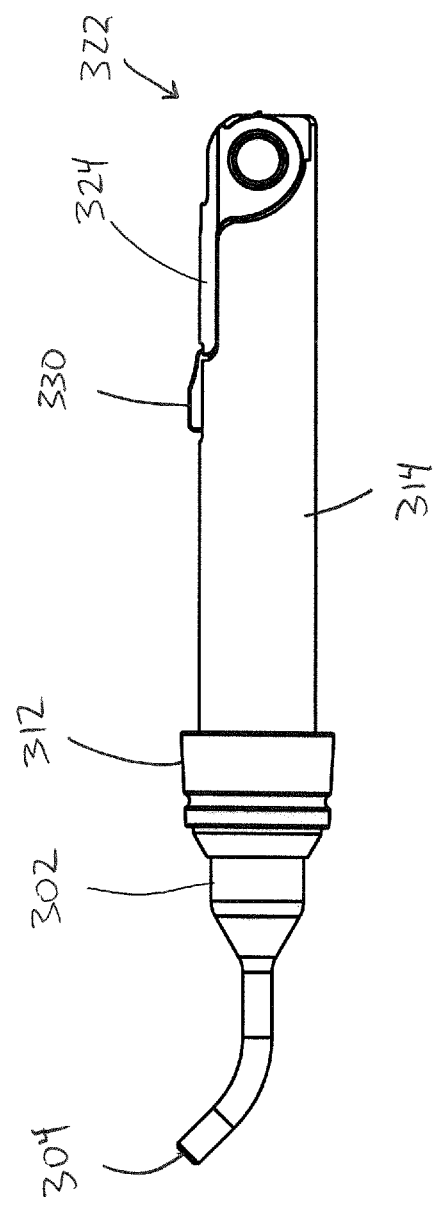
FIG. 19B is a perspective view of the tensioning instrument of FIG. 18 in the locked and preloaded configurations.

The locking mechanism 240 is of similar construction to that disclosed in U.S. patent application Ser. No. 13/730,597, filed Dec. 28, 2012, which is incorporated by reference herein in its entirety. In particular, the locking mechanism includes a lever 242, which is mounted on an inner cylindrical member 244 for rotating the inner cylindrical member. An outer annular member 246 is partially rotatably mounted on the inner cylindrical member 244 with a limited amount of play to assist with locking the cable which extends through openings 248, 250 in both the inner cylindrical member 244 and the outer annular member 246, which are aligned when the locking mechanism is in the unlocked or release configuration, as shown in FIG. 16. When the lever 242 is rotated distally, the openings 248, 250 will become slightly misaligned, thereby crimping the cable between the openings as described in U.S. patent application Ser. No. 13/730,597. The locking mechanism 240 includes a release mechanism 252 including spring loaded buttons 254, 256 which engage with movable shafts 257 which lock the lever 242 in the closed, locked position until the buttons are depressed to release the locking lever 242

In operation, the cable is inserted through the distal tip 220 and strung through the body of the instrument and through the openings 248, 250 of the locking mechanism 240. The lever is the rotated from the load or release configuration shown in FIG. 12B to the locked configuration shown in FIG. 12A, thereby locking the cable in place. The tensioning screw 210 is then rotated by a driver, either manually or with a power tool. Advantageously, the tensioning screw may be provided with a head that is identical to the bone screws used in attaching a bone plate to the bone, such that the same driver may be used. As the tensioning screw is rotated, the annular ring member 230 is driven proximally on the threaded proximal portion 228 of the shaft, thereby compressing tensioning spring 236 and applying tension to the cable. Once the desired tension is achieved as indicated by the indicator 237 on the scale 258 disposed on the lever 242, the instrument 200 may be left in place as other cables are being tensioned. Thus, if the tension in one cable changes as other cables are tensioned, the user may simply apply the driver once more and adjust the tension as needed. Once all of the cables are appropriately tensioned and locked or crimped, the instrument may be removed by depressing the buttons 254 of the release mechanism 252 to release the cable and simply pull the instrument 200 away from the cable. Advantageously, the instrument 200 is configured to be relatively small, i.e. can fit in the palm of the user's hand, or is less than 4 inches long from the distal tip 220 to the proximal end. In one form, the instrument is approximately 3¼ inches long with the lever 242 in the closed position. Moreover, because it may be left in place while other cables are tensioned, no retensioner is needed.

Figure 20:
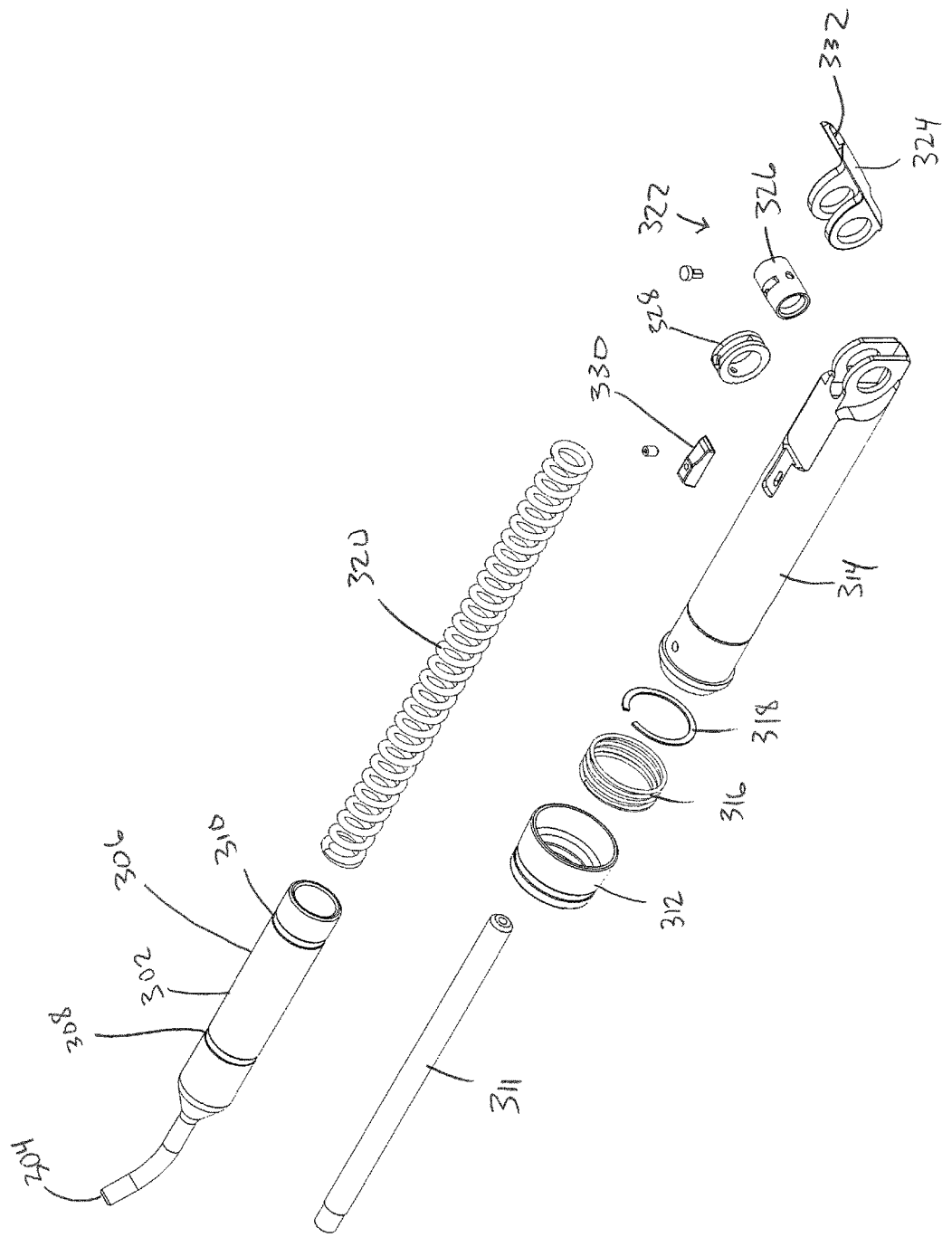
FIG. 20 is an exploded perspective view of the tensioning instrument of FIG. 18.

Another tensioning instrument in accordance with the present invention is disclosed in FIGS. 18-22B. As shown in FIGS. 18 and 20, the instrument 300 includes distal housing member 302 with a hollow cylindrical portion 306 and a distal end portion 304. The outer surface of the hollow cylindrical portion 306 includes distal and proximal annular grooves 308, 310 for engaging with mating balls 313, 315 (FIGS. 22A, 22B) of the actuator mechanism, which includes sleeve 312, which is operably connected to the proximal housing member 314 and is spring biased in the distal direction by spring 316 against retaining ring 318. A narrower bore shaft member 311 is operably connected to the interior of the distal housing member 302 for protecting the cable from the spring 320.

The proximal housing member 314 has a generally cylindrical configuration with a hollow interior for housing tensioning spring 320 therein. A locking mechanism 322 is located at a proximal end of the housing member 314 having a similar configuration to the locking mechanism 240 shown in FIGS. 12A-17, except the release mechanism takes a different configuration. Accordingly, description of the lever 324, inner cylindrical member 326, and outer annular member 328 and other related components is omitted for sake of brevity. The release mechanism takes the form of a slide lock member 330 mounted to the proximal housing member 314, which slides over a mating portion 332 of the lever 324 to lock the lever in place once the lever is rotated into the locked configuration (See FIGS. 19B, 22B). The lever 324 is released by sliding the slide lock member 330 distally.

Figure 22A:
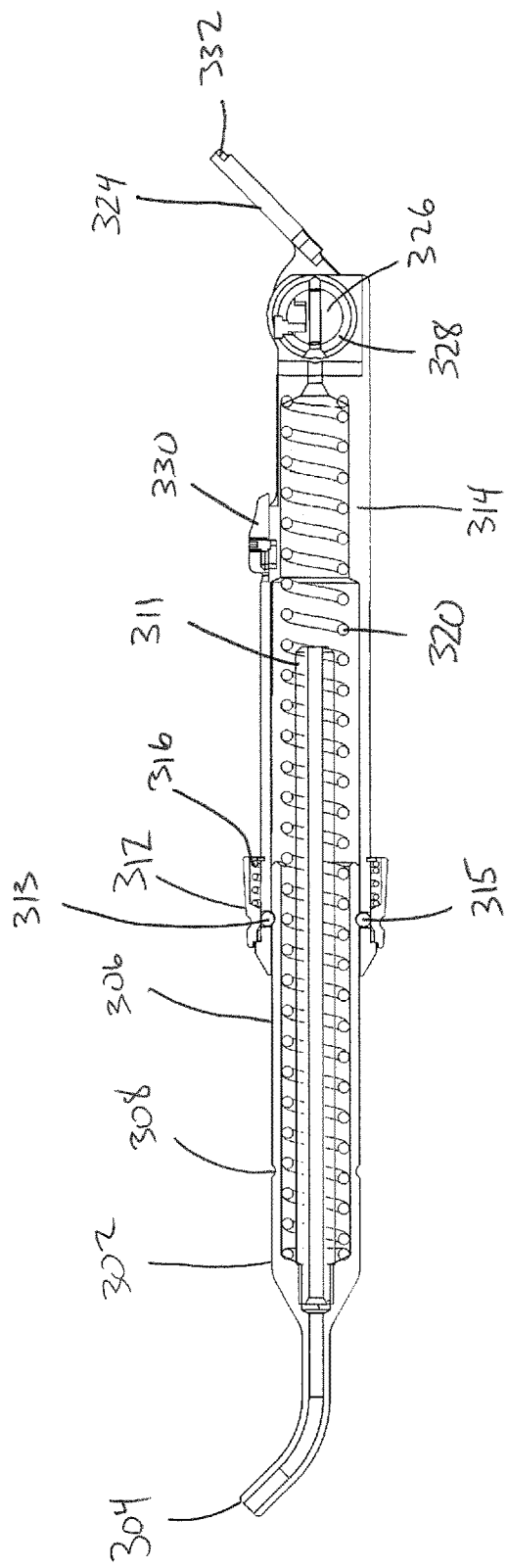
FIG. 22A is a side cross-sectional view of the tensioning instrument of FIG. 18 in the unlocked or release configuration and the unloaded configuration taken along the superior-inferior plane along the longitudinal instrument axis.
Figure 22B:
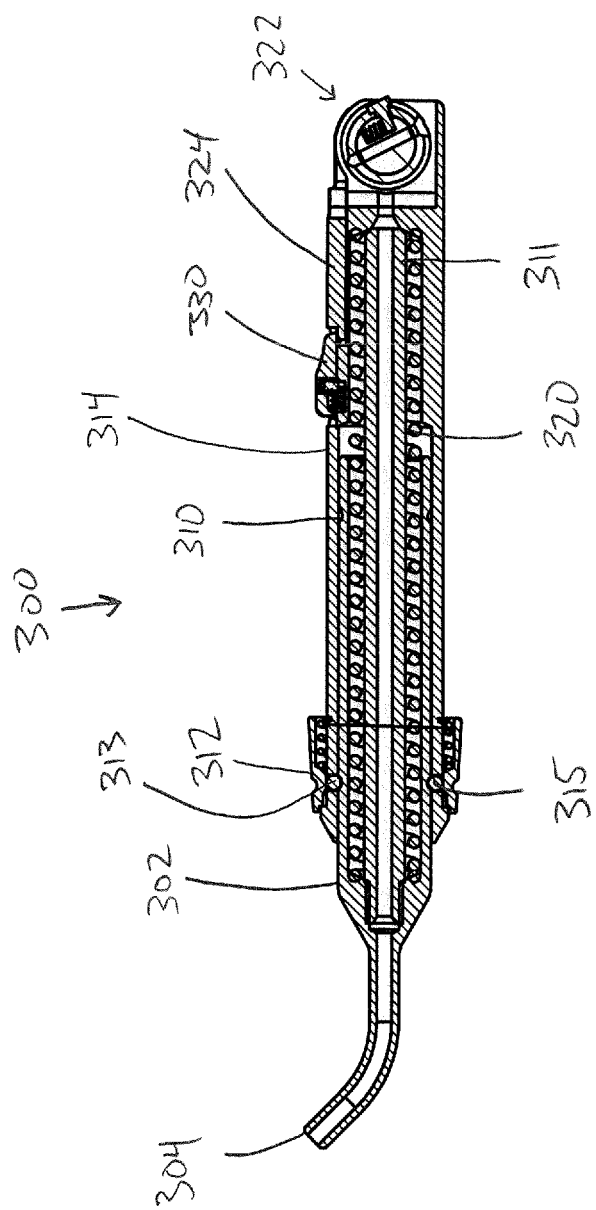
FIG. 22B is a side cross-sectional view of the tensioning instrument of FIG. 18 in the locked and preloaded configurations taken along the superior-inferior plane along the longitudinal instrument axis.

With reference to FIGS. 22A and 22B, the tensioning instrument 300 is initially in an unloaded configuration as shown in FIG. 22A, wherein the spring 220 is uncompressed. The instrument is then preloaded with the predetermined amount of tension, which is determined by factors including the spring used and distance between the annular grooves 308, 310, i.e., the amount of compression of the spring. To preload the instrument 300, the sleeve 312 is shifted proximally to allow the balls captured in the annular groove 310 to be displaced outwardly, thereby allowing the distal housing member 302 and the proximal housing member 314 to move relative to one another. The housing members 302, 314 may then be urged together against the resistance of the spring 320 until the balls of the release mechanism become captured in the distal annular groove 308, thereby locking the housing members 302, 314 with respect to one another with the spring 320 in a compressed configuration. The cable may then be inserted through the passageway in the instrument 300 through the distal tip 304 and through the locking mechanism 322. The locking mechanism is then moved from the loading or release configuration into the locked configuration by rotating the lever 332 to be flush against the proximal housing member 314 and sliding the slide lock member 330 over the mating portion of the lever 324 to lock the lever in place. With the cable now locked, the user may then release the actuator sleeve 312 by pulling it proximally, thereby applying the biasing force of the spring 320 to the cable, such that now the cable prevents expansion of the housing members 302, 314 apart from one another, which tensions the cable. Thus, provided there is little or no slack in the cable, the instrument 300 will not expand significantly and will not return to the initial unloaded configuration until the cable is released from the locking mechanism 322. Further, given the relatively long length of the spring 320, small variations in the displacement of the spring, e.g., due to slack in the cable prior to tensioning, will have minimal effect on the amount of tension applied to the cable. Accordingly, the instrument will consistently apply the desired amount of tension.

Accordingly, the instrument 300 applies a predetermined amount of tension to the cable without need for a retensioner or any adjustment once the instrument is attached to the cable and tension has been applied. Further, the instrument may be preloaded by a surgical technician, reducing the amount of time needed to tension the cables. Provided that the instrument is left in place while other cables are tensioned, the spring will compensate for any changes in tension in the cable automatically and thereby eliminate the need for a retensioner.

Another tensioning instrument in accordance with the present invention is disclosed in FIGS. 23-26. The instrument 400 is preferably of unitary construction and formed from a resilient material, and preferably a superelastic material such as nitinol. The instrument has first and second leg portions 402, 404, which are connected via a hinge portion 406, which has a generally arcuate configuration. In the expanded configuration of the instrument, the leg portions 402, 404 are preferably splayed apart by approximately 90 degrees, although other configurations are possible. The legs 402, 404 may be compressed together by a tool to put the instrument in the compressed configuration.

The first leg portion 402 includes a single aperture 408 through which the cable 422 is initially fed. The cable 422 is then thread through a pair or apertures 410, 412 in the second leg portion 404. The longitudinal axes of the apertures 410, 412 in the second leg portion 404 are preferably oriented to be transverse to one another such that the cable 422 is cinched and held in place when the cable passes therethrough. In particular, the opening of the first aperture 410 on the inner facing surface 414 of the second leg portion 404 is located further from the hinge 406 than the opening of the first aperture 410 in the outer facing surface 416 of the second leg portion 404. Similarly, the opening of the second aperture 412 on the inner facing surface 414 of the second leg portion 404 is located closer to the hinge 406 than the opening of the second aperture 412 in the outer facing surface 416 of the second leg portion 404. In other words, the apertures 410, 412 diverge from one another as they extend through the thickness of the second leg portion 410 from the inner facing surface 414 to the outer facing surface 416. Given that the cable is sufficiently thick relative to the apertures' size, the circuitous or divergent path provided by the apertures 410, 412 will capture the cable when tension is applied by the user or by expansion of the leg portions 402, 404 apart from one another. This way no further locking mechanism is needed, thereby simplifying manufacture and use of the instrument 400.

Figure 23:
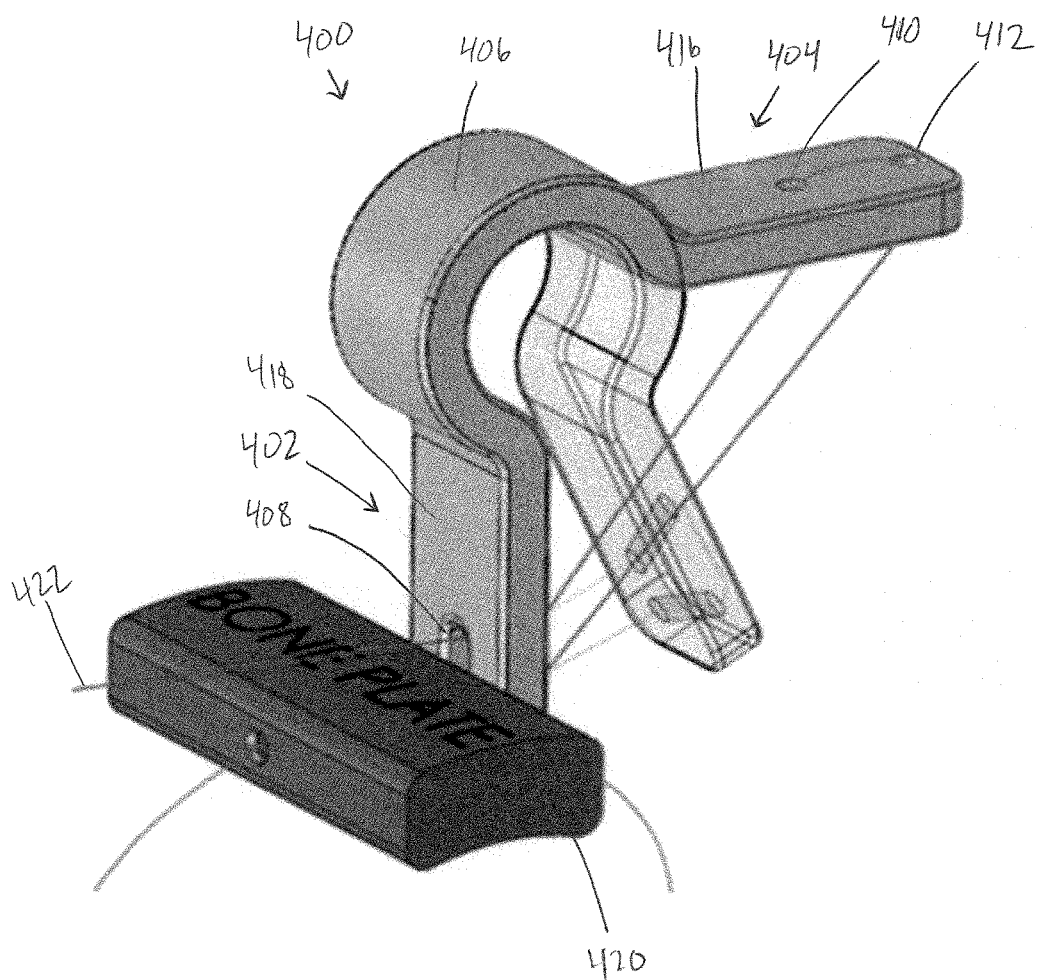
FIG. 23 is a perspective view of an alternate tensioning instrument demonstrating a compressed and an expanded configuration in accordance with the present invention.
Figure 24:
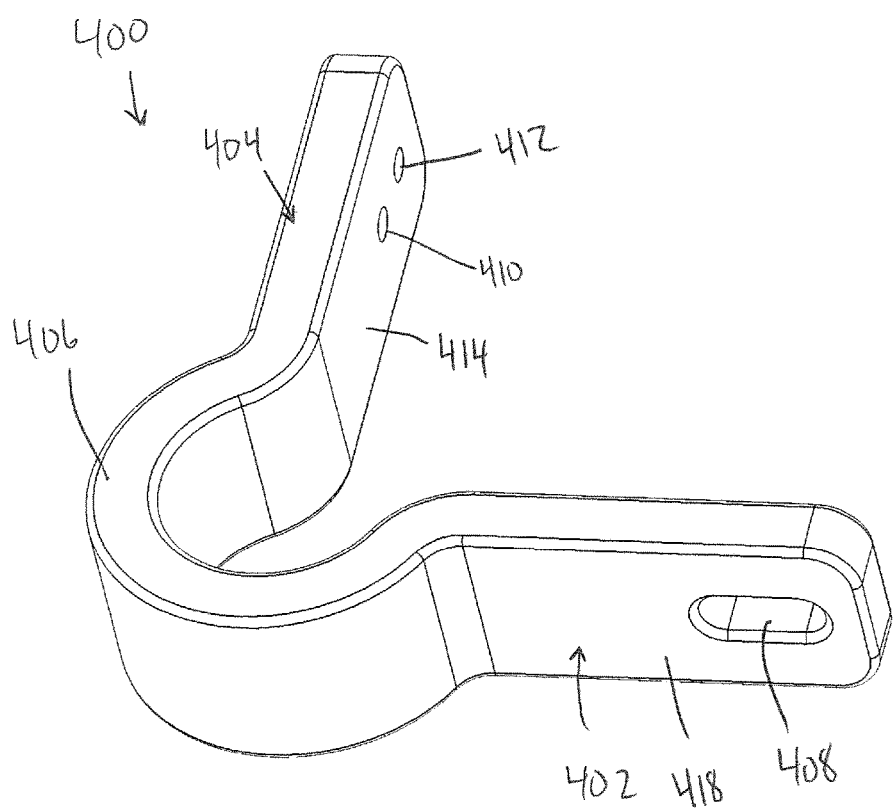
FIG. 24 is a perspective view of the tensioning instrument of FIG. 23 in the expanded configuration.
Figure 75:
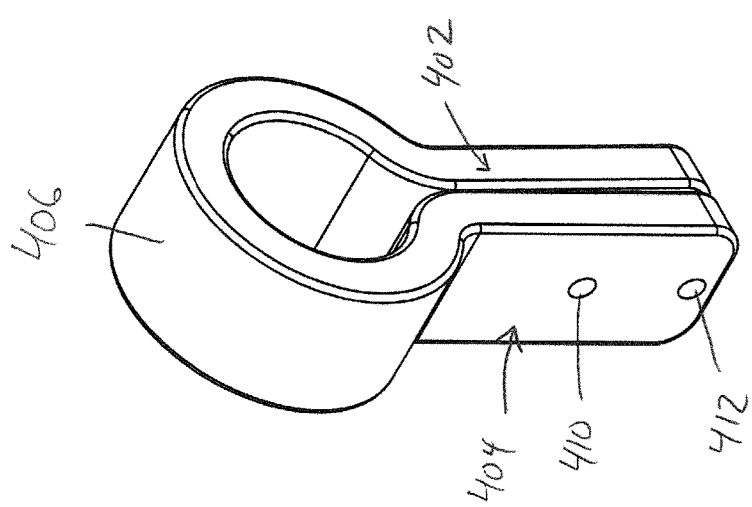
Figure 26:
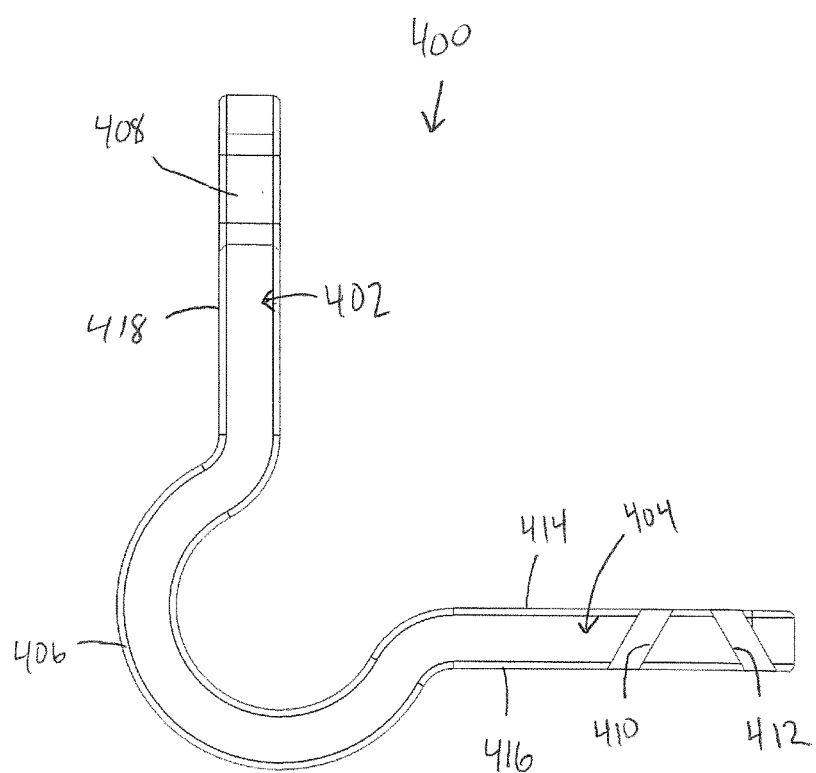
FIG. 26 is a side cross-sectional view of the tensioning instrument of FIG. 23 taken along the superior-inferior plane through the centerline of the instrument.

In operation, as shown in FIG. 23, the instrument 400 is first compressed by an inserter instrument and then the cable 422 is fed through the aperture 408 in the first leg portion. The cable 422 is then fed through the second aperture 412 and then back through the first aperture 410 and returning back through the aperture 408 in the first leg portion 402. The outer surface 418 of the first leg portion 402 is abutted against the bone plate 420 and the cable is pulled taught manually. Next, the instrument releases the second leg portion 404 while the first leg portion 402 is abutted against the bone plate 420. Due to the resilience of the material, the second leg portion 404 will be urged away from the first leg portion 402 thereby pulling on and tensioning the cable 422 with a predetermined amount of force determined by the resiliency of the material. The instrument 400 may be left in place while other instruments 400 are used to tension other cables, and no retensioning will be necessary, as the resiliency of the material will automatically compensate for changes in tension when other cables are applied to the bone or bone plate. Due to the simplicity of the instrument 400, the instrument may be easily cleaned and reused if desired.

Those skilled in the art would recognize that a wide variety of modifications, alterations, and combinations can be made with respect to the above described embodiments without departure from the spirit and scope of the invention, in that such modifications, alterations, and combinations, are to be viewed as being within the scope of the invention.

What is claimed is:

1. A cable-tensioning instrument, comprising:
a body including a distal member having a distal tip with an opening for receiving a cable;
a passageway extending along a longitudinal axis from the distal tip opening to a proximal end opening for receiving a cable to be tensioned therethrough;
a rotatable drive shaft disposed within the instrument body;
an actuator for rotating the drive shaft;
a traveler member mounted to the drive shaft and configured to shift longitudinally therealong when the drive shaft is rotated by the actuator;
a proximal member of the body movably connected to the distal member for being longitudinally shifted by the traveler member away from the distal member and distal tip thereof; and
a locking mechanism configured to fix a cable thereto, the locking mechanism carried on the proximal member of the body and rotatable relative to the proximal member;
wherein the traveler member urges the proximal member of the body and the locking mechanism carried thereon away from the distal tip to tension the cable fixed to the locking mechanism when the actuator is actuated.

2. The cable-tensioning instrument of claim 1, further comprising a biasing member operably engaged with the traveler member and the proximal member for providing a biasing force operable to urge the locking mechanism proximally away from the distal tip for applying tension to the cable.

3. The cable-tensioning instrument of claim 1, further comprising a tension indicator connected to the traveler member for indicating the amount of tension applied to the cable.

4. The cable-tensioning instrument of claim 3, wherein the locking mechanism includes a lever with an opening disposed therein for receiving at least a portion of the tension indicator with the lever in a closed position corresponding with a locked configuration of the locking mechanism.

5. The cable-tensioning instrument of claim 1, wherein an entirety of the instrument is sized and configured to fit within a palm of a user's hand.

6. A cable-tensioning instrument comprising:
a body including a distal tip having an opening for receiving a cable;
a passageway extending along a longitudinal axis from the distal tip opening to a proximal end opening for receiving a cable to be tensioned therethrough;
a rotatable drive shaft disposed within the instrument body;
an actuator for rotating the drive shaft;
a traveler member mounted to the drive shaft and configured to shift therealong when the drive shaft is rotated by the actuator; and
a locking mechanism configured to fix a cable thereto, the locking mechanism operably engaged with the traveler member for being shifted along the longitudinal axis thereby;
wherein the traveler member urges the locking mechanism away from the distal tip to tension the cable fixed to the locking mechanism when the actuator is actuated;
wherein the drive shaft has a threaded portion and the traveler member has a mating threaded portion for engaging with the threaded portion of the drive shaft to shift the traveler member therealong when the drive shaft is rotated by the actuator.

7. A cable-tensioning instrument comprising:
a body including a distal tip having an opening for receiving a cable;
a passageway extending along a longitudinal axis from the distal tip opening to a proximal end opening for receiving a cable to be tensioned therethrough;
a rotatable drive shaft disposed within the instrument body;
an actuator for rotating the drive shaft;
a traveler member mounted to the drive shaft and configured to shift therealong when the drive shaft is rotated by the actuator;
a locking mechanism configured to fix a cable thereto, the locking mechanism operably engaged with the traveler member for being shifted along the longitudinal axis thereby;
wherein the traveler member urges the locking mechanism away from the distal tip to tension the cable fixed to the locking mechanism when the actuator is actuated; and
a distal member of the instrument body having the distal tip and a proximal portion including a longitudinally oriented slot;
wherein the traveler member includes an index portion which engages with the longitudinally oriented slot to inhibit rotation of the traveler member when the drive shaft is rotated so that the traveler member translates along a length of the drive shaft when the drive shaft is rotated.

8. The cable-tensioning instrument of claim 7, further comprising a proximal member of the instrument body including the locking mechanism;
wherein the proximal portion of the distal member includes a smooth outer surface for being received in and slidingly engaging with a corresponding interior portion of the proximal member such that the proximal and distal members are configured to shift with respect to one another along the longitudinal axis for applying tension to the cable.

9. The cable-tensioning instrument of claim 7, wherein the actuator comprises a rotary member having a drive head for engaging with a mating tool to be rotated thereby, the rotary member operably connected to the distal member and the drive shaft for rotating the drive shaft via a corresponding rotation of the rotary member.

10. The cable-tensioning instrument of claim 9, further comprising a drive gear connected to the rotary member and a mating driven gear connected to the drive shaft, the drive and driven gears in operable engagement such that rotation of the rotary member causes a corresponding rotation of the gears and the drive shaft.

11. A cable-tensioning instrument comprising:
a body including a distal tip having an opening for receiving a cable;
a passageway extending along a longitudinal axis from the distal tip opening to a proximal end opening for receiving a cable to be tensioned therethrough;
a rotatable drive shaft disposed within the instrument body;
an actuator for rotating the drive shaft;
a traveler member mounted to the drive shaft and configured to shift therealong when the drive shaft is rotated by the actuator; and a locking mechanism configured to fix a cable thereto, the locking mechanism operably engaged with the traveler member for being shifted along the longitudinal axis thereby;

wherein the traveler member urges the locking mechanism away from the distal tip to tension the cable fixed to the locking mechanism when the actuator is actuated;

wherein the drive shaft includes a longitudinally-oriented passage extending therethrough and forms at least part of the passageway for receiving the cable therein.

\* \* \* \* \*